United States Patent

Seitz et al.

(10) Patent No.: US 8,916,501 B2
(45) Date of Patent: Dec. 23, 2014

(54) HERBICIDAL COMPOSITIONS

(75) Inventors: Thomas Seitz, Viernheim (DE); Trevor William Newton, Neustadt (DE); Anja Simon, Weinheim (DE); Richard Roger Evans, Limburgerhof (DE); Andreas Landes, Roemerberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/993,943

(22) PCT Filed: Dec. 13, 2011

(86) PCT No.: PCT/EP2011/072596
§ 371 (c)(1),
(2), (4) Date: Jun. 13, 2013

(87) PCT Pub. No.: WO2012/080239
PCT Pub. Date: Jun. 21, 2012

(65) Prior Publication Data
US 2013/0267417 A1 Oct. 10, 2013

(30) Foreign Application Priority Data
Dec. 15, 2010 (EP) .................................. 10195216

(51) Int. Cl.
*A01N 25/26* (2006.01)
*A01N 25/32* (2006.01)
*A01N 43/84* (2006.01)

(52) U.S. Cl.
CPC ............... *A01N 25/32* (2013.01); *A01N 43/84* (2013.01)
USPC ............ 504/100; 504/103; 504/112; 504/225

(58) Field of Classification Search
CPC .................................................... A01N 43/66
See application file for complete search history.

(56) References Cited

U.S. PATENT DOCUMENTS

| 5,080,710 A | 1/1992 | Rueb et al. |
| 5,215,570 A | 6/1993 | Burckhardt et al. |
| 5,529,974 A | 6/1996 | Kerber |
| 5,532,203 A | 7/1996 | Foery et al. |
| 6,235,680 B1 * | 5/2001 | Ziemer et al. ............... 504/112 |
| 8,445,407 B2 | 5/2013 | Witschel et al. |
| 2011/0015068 A1 * | 1/2011 | Sievernich et al. ........... 504/134 |
| 2011/0086762 A1 | 4/2011 | Fischer et al. |
| 2013/0102463 A1 * | 4/2013 | Ehrhardt et al. .............. 504/103 |

FOREIGN PATENT DOCUMENTS

| CN | 1687061 | 10/2005 |
| CN | 100386324 | 5/2008 |
| EP | 0 170 191 | 2/1986 |
| EP | 0 365 484 | 10/1989 |
| EP | 0 413 832 | 2/1991 |
| EP | 2 103 615 | 9/2009 |
| JP | 200 247975 | 9/2012 |
| WO | WO 90/06748 | 6/1990 |
| WO | WO 90/10626 | 8/1990 |
| WO | WO 92/06962 | 4/1992 |
| WO | WO 93/15074 | 8/1993 |
| WO | WO 94/03454 | 2/1994 |
| WO | WO 97/07104 | 2/1997 |
| WO | WO 97/45016 | 12/1997 |
| WO | WO 02/066471 | 8/2002 |
| WO | WO 2010/003444 | 1/2010 |
| WO | WO 2010/040485 | 4/2010 |
| WO | WO 2010/051393 | 5/2010 |
| WO | WO 2010145992 | * 6/2010 |
| WO | WO 2010/145992 | 12/2010 |
| WO | WO 2011/018486 | 2/2011 |
| WO | WO 2011018486 | * 2/2011 |
| WO | WO 2011/057935 | 5/2011 |
| WO | WO 2012/041789 | 4/2012 |

OTHER PUBLICATIONS

International Search Report dated Apr. 24, 2012, prepared in International Application No. PCT/EP2011/072596.

International Preliminary Report on Patentability dated Jun. 18, 2013, prepared in International Application No. PCT/EP2011/072596.

Haga et al., "Acid-Catalyzed Amino-Migration of O-Phenylhydroxylamines", J. Am. Chem. Soc., vol. 114, 1992, pp. 9795-9806.

Office Action dated Sep. 13, 2013 in Co-pending U.S Appl. No. 13/378,137, filed Dec. 14, 2011.

Office Action dated Jul. 31, 2013 in Co-pending U.S. Appl. No. 13/876,330, filed Dec. 14, 2011.

* cited by examiner

*Primary Examiner* — Alton Pryor
(74) *Attorney, Agent, or Firm* — Brinks Gilson & Lione

(57) ABSTRACT

The present invention relates to a herbicidal composition comprising:

A) at least one benzoxazinone compound of the formula I wherein the variables are as defined as given in the specification;
and a safener of formula II as defined in the specification.

15 Claims, No Drawings

HERBICIDAL COMPOSITIONS

This application is a National Stage application of International Application No. PCT/EP2011/072596, filed Dec. 13, 2011, the entire contents of which is hereby incorporated herein by reference. This application also claims priority under 35 U.S.C. §119 to European Patent Application No. 10195216.6, filed Dec. 15, 2010, the entire contents of which is hereby incorporated herein by reference.

The present invention relates to herbicidal compositions comprising at least a benzoxazinone of the general formula I and a safener of formula II. Moreover, the invention relates to a method for controlling unwanted vegetation.

In crop protection products, it is desirable in principle to increase the specificity and the reliability of the action of active compounds. In particular, it is desirable for the crop protection product to control the harmful plants effectively and, at the same time, to be tolerated by the useful plants in question. It is known that in some cases better crop plant compatibility can be achieved by joint application of specifically acting herbicides with organic active compounds, which act as antidotes or antagonists. Owing to the fact that they can reduce or even prevent damage to the crop plants, they are also referred to as safeners.

Safeners of formula II are inter alia known from EP 365 484, EP 2 103 615 and WO 10/040,485.

WO 02/066471 describes structurally similar compounds for which herbicidal action is stated, which differ from the benzoxazinone I according to the present invention that the benzo[1,4]oxazine ring is unsubstituted in the 2-position, whereas the benzoxazinone of formula I according to the present invention are substituted in said position by at least one halogen atom.

However, the herbicidal properties of these known compounds with regard to the harmful plants, and their compatibility with crop plants are not always entirely satisfactory.

It is therefore an object of the present invention to provide herbicidal compositions, which are highly active against unwanted harmful plants. At the same time, the compositions should have good compatibility with useful plants. In addition, the compositions according to the invention should have a broad spectrum of activity.

This and further objects are achieved by the herbicidal active compositions below.

Accordingly, the present invention also relates to herbicidal active compositions comprising:

A) a benzoxazinone of the formula I

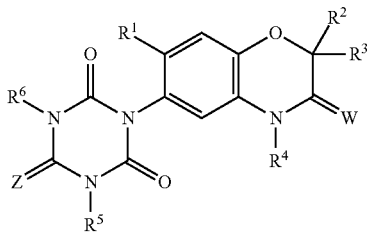

wherein
$R^1$ is hydrogen or halogen;
$R^2$ is halogen;
$R^3$ is hydrogen or halogen;
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is hydrogen, $NH_2$, $C_1$-$C_6$-alkyl or $C_3$-$C_6$-alkynyl;
$R^6$ is hydrogen or $C_1$-$C_6$-alkyl; and
W is O or S;
Z is O or S; and
B) a safener of formula II

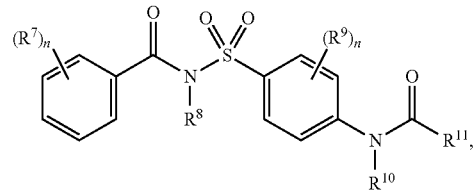

wherein
n is 1 to 5;
$R^7$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^8$ is hydrogen or $C_1$-$C_6$-alkyl;
$R^9$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^{10}$ is hydrogen or $C_1$-$C_6$-alkyl; and
$R^{11}$ is hydrogen, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, $C_1$-$C_6$-alkylthio, $C_1$-$C_6$-alkylamino, di($C_1$-$C_6$-alkyl)amino, $C_3$-$C_6$-cycloalkylamino or $C_3$-$C_6$-cycloalkyl.

The present invention also provides the use of compositions comprising at least a benzoxazinone of formula I and a safener of formula II, i.e. for controlling harmful plants.

The present invention also provides formulated compositions comprising at least a benzoxazinone of formula I and a safener of formula II, and auxiliaries customary for formulating crop protection agents.

The present invention furthermore provides a method for controlling unwanted vegetation where a herbicidal effective amount of the compositions comprising at least a benzoxazinone of formula I and a safener of formula II is allowed to act on plants, their seeds and/or their habitat.

The invention furthermore relates to a method for controlling unwanted vegetation, in particular where crop plants are cultivated.

As used herein, the terms "controlling" and "combating" are synonyms.

As used herein, the terms "undesirable vegetation" and "harmful plants" are synonyms.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables $R^1$ to $R^{11}$, are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl and also the $C_1$-$C_4$-alkyl moieties of $C_3$-$C_6$-cycloalkyl-$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkylamino and $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of hydroxycarbonyl-$C_1$-$C_4$-alkoxy, $C_1$-$C_6$-alkoxycarbonyl-$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-haloalkoxy and $C_1$-$C_6$-alkyoxy-$C_1$-$C_6$-alkyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylamino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$-$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_6$-alkyl)amino: di($C_1$-$C_4$-alkyl)amino as mentioned above, and also, for example, N,N-dipentylamino, N,N-dihexylamino, N-methyl-N-pentylamino, N-ethyl-N-pentylamino, N-methyl-N-hexylamino and N-ethyl-N-hexylamino.

The preferred embodiments of the invention mentioned herein below have to be understood as being preferred either independently from each other or in combination with one another.

According to a preferred embodiment of the invention preference is given to those benzoxazinones of formula I, wherein the variables, either independently of one another or in combination with one another, have the following meanings:

$R^1$ is hydrogen;
  is also preferably halogen, particularly preferred F or Cl, especially preferred F;

$R^2$ is F;

$R^3$ is hydrogen or F, preferably hydrogen;
  is also preferably halogen, particularly preferred F;

$R^4$ is $C_3$-$C_6$-alkynyl or $C_3$-$C_6$-halolkynyl, preferably $C_3$-alkynyl or $C_3$-halolkynyl, particularly preferred $CH_2C\equiv CH$, $CH_2C\equiv CCl$ or $CH_2C\equiv CBr$;
  is also preferably $C_3$-$C_6$-alkynyl or $C_3$-$C_6$-cycloalkyl-$C_1$-$C_6$-alkyl, particularly preferred propargyl or cyclopropylmethyl;
  is also preferably $C_3$-$C_6$-alkynyl, preferably $C_3$-alkynyl; particularly preferred $CH_2C\equiv CH$;
  is also preferably $C_3$-$C_6$-halolkynyl, preferably $C_3$-halolkynyl, particularly preferred $CH_2C\equiv CCl$ or $CH_2C\equiv CBr$;

$R^5$ is $NH_2$, $C_1$-$C_6$-Alkyl or $C_3$-$C_6$-alkynyl; preferably $C_1$-$C_6$-alkyl; more preferably $C_1$-$C_4$-alkyl; most preferably $CH_3$;

$R^6$ is $C_1$-$C_6$-alkyl; preferably $C_1$-$C_4$-alkyl; most preferably $CH_3$;

W is O,
  is also preferably S;

Z is O,
  is also preferably S.

Particular preference is given to the benzoxazinone of the formula I.a (corresponds to formula I wherein $R^2$ is F, $R^5$ and $R^6$ are $CH_3$, W is O and Z is S),

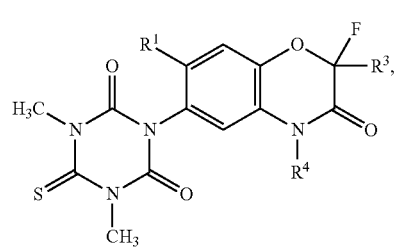

I.a wherein the variables $R^1$, $R^3$, and $R^4$ have the meanings, in particular the preferred meanings, as defined above;
most preference to the benzoxazinones of the formulae I.a.1 to I.a.54 of Table A listed below, in which the variables $R^1$, $R^3$ and $R^4$ together have the meanings given in one row of Table A (benzoxazinones I.a.1 to I.a.54); and where the definitions of the variables $R^1$, $R^2$, $R^3$ and $R^4$ are of particular importance for the compounds according to the invention not only in combination with one another but in each case also on their own:

TABLE A

| No. | $R^1$ | $R^3$ | $R^4$ |
|---|---|---|---|
| I.a.1. | H | H | H |
| I.a.2. | H | H | $CH_3$ |
| I.a.3. | H | H | $C_2H_5$ |
| I.a.4. | H | H | $CH_2$—$C_2H_5$ |
| I.a.5. | H | H | $CH(CH_3)_2$ |
| I.a.6. | H | H | $CH_2$—$CH_2$—$(CH_3)_2$ |
| I.a.7. | H | H | $CH_2$—$CH\equiv CH_2$ |
| I.a.8. | H | H | $CH_2C\equiv CH$ |
| I.a.9. | H | H | $CH_2C\equiv C$—Br |
| I.a.10. | H | F | H |
| I.a.11. | H | F | $CH_3$ |
| I.a.12. | H | F | $C_2H_5$ |
| I.a.13. | H | F | $CH_2$—$C_2H_5$ |
| I.a.14. | H | F | $CH(CH_3)_2$ |
| I.a.15. | H | F | $CH_2$—$CH_2$—$(CH_3)_2$ |
| I.a.16. | H | F | $CH_2$—$CH\equiv CH_2$ |
| I.a.17. | H | F | $CH_2C\equiv CH$ |

TABLE A-continued

| No. | $R^1$ | $R^3$ | $R^4$ |
|---|---|---|---|
| I.a.18. | H | F | $CH_2C\equiv C-Br$ |
| I.a.19. | F | H | H |
| I.a.20. | F | H | $CH_3$ |
| I.a.21. | F | H | $C_2H_5$ |
| I.a.22. | F | H | $CH_2-C_2H_5$ |
| I.a.23. | F | H | $CH(CH_3)_2$ |
| I.a.24. | F | H | $CH_2-CH_2-(CH_3)_2$ |
| I.a.25. | F | H | $CH_2-CH=CH_2$ |
| I.a.26. | F | H | $CH_2C\equiv CH$ |
| I.a.27. | F | H | $CH_2C\equiv C-Br$ |
| I.a.28. | F | F | H |
| I.a.29. | F | F | $CH_3$ |
| I.a.30. | F | F | $C_2H_5$ |
| I.a.31. | F | F | $CH_2-C_2H_5$ |
| I.a.32. | F | F | $CH(CH_3)_2$ |
| I.a.33. | F | F | $CH_2-CH_2-(CH_3)_2$ |
| I.a.34. | F | F | $CH_2-CH=CH_2$ |
| I.a.35. | F | F | $CH_2C\equiv CH$ |
| I.a.36. | F | F | $CH_2C\equiv C-Br$ |
| I.a.37. | Cl | H | H |
| I.a.38. | Cl | H | $CH_3$ |
| I.a.39. | Cl | H | $C_2H_5$ |
| I.a.40. | Cl | H | $CH_2-C_2H_5$ |
| I.a.41. | Cl | H | $CH(CH_3)_2$ |
| I.a.42. | Cl | H | $CH_2-CH_2-(CH_3)_2$ |
| I.a.43. | Cl | H | $CH_2-CH=CH_2$ |
| I.a.44. | Cl | H | $CH_2C\equiv CH$ |
| I.a.45. | Cl | H | $CH_2C\equiv C-Br$ |
| I.a.46. | Cl | F | H |
| I.a.47. | Cl | F | $CH_3$ |
| I.a.48. | Cl | F | $C_2H_5$ |
| I.a.49. | Cl | F | $CH_2-C_2H_5$ |
| I.a.50. | Cl | F | $CH(CH_3)_2$ |
| I.a.51. | Cl | F | $CH_2-CH_2-(CH_3)_2$ |
| I.a.52. | Cl | F | $CH_2-CH=CH_2$ |
| I.a.53. | Cl | F | $CH_2C\equiv CH$ |
| I.a.54. | Cl | F | $CH_2C\equiv C-Br$ |

An especially preferred benzoxazinone of the formula I which, as component A, is part of the composition according to the invention, is the benzoxazinone of formula I.a.35 as defined above:

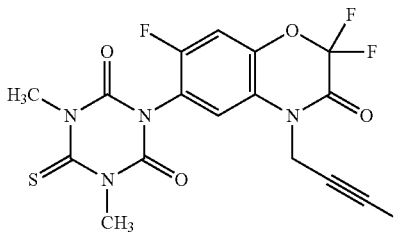

I.a.35

According to a preferred embodiment of the invention preference is given to those safeners of formula II, wherein the variables, either independently of one another or in combination with one another, have the following meanings:

n is 1 or 2;
  is preferably 1; is also preferably 2;
$R^7$ is $C_1$-$C_6$-alkyl or $C_1$-$C_6$-alkoxy;
  is preferably $C_1$-$C_4$-alkyl or $C_1$-$C_4$-alkoxy;
  is also preferably $C_1$-$C_6$-alkyl, particularly preferred $C_1$-$C_4$-alkyl;
  is also preferably $C_1$-$C_6$-alkoxy, particularly preferred $C_1$-$C_4$-alkoxy;
$R^8$ is hydrogen;
  is also preferably $C_1$-$C_6$-alkyl, particularly preferred $C_1$-$C_4$-alkyl;

$R^9$ is hydrogen;
$R^{10}$ is hydrogen;
  is also preferably $C_1$-$C_6$-alkyl, particularly preferred $C_1$-$C_4$-alkyl;
$R^{11}$ is $C_1$-$C_6$-alkyl, $C_1$-$C_6$-alkoxy-$C_1$-$C_6$-alkyl, $C_1$-$C_6$-alkoxy, $C_1$-$C_6$-alkylthio, $C_1$-$C_6$-alkylamino, di($C_1$-$C_6$-alkyl)amino or $C_3$-$C_6$-cycloalkyl;
  is preferably $C_1$-$C_6$-alkylamino, di($C_1$-$C_6$-alkyl)amino or $C_3$-$C_6$-cycloalkyl;
  is particularly preferred $C_1$-$C_6$-alkylamino or di($C_1$-$C_6$-alkyl)amino;
  is especially preferred $C_1$-$C_6$-alkylamino;
  is mostly preferred $C_1$-$C_4$-alkylamino.

Particular preference is given to the safeners of the formula II.a (corresponds to formula II wherein $R^8$, $R^9$ and $R^{10}$ are hydrogen),

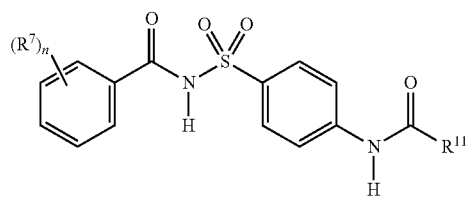

II.a wherein the variables n, $R^7$ and $R^{11}$ have the meanings, in particular the preferred meanings, as defined above; most preference to the safeners of the formulae II.a.1 to II.a.34 of Table B listed below, in which the variables n, $R^7$ and $R^{11}$ together have the meanings given in one row of Table B (safeners II.a.1 to II.a.34); and where the definitions of the variables n, $R^7$ and $R^{11}$ are of particular importance for the compounds according to the invention not only in combination with one another but in each case also on their own:

TABLE B

| No. | n | $R^7$ | $R^{11}$ |
|---|---|---|---|
| II.a.1 | 1 | (2)-$OCH_3$ | —$CH_3$ |
| II.a.2 | 1 | (2)-$OCH_3$ | —$C_2H_5$ |
| II.a.3 | 1 | (2)-$OCH_3$ | -n-$C_3H_7$ |
| II.a.4 | 1 | (2)-$OCH_3$ | -iso-$C_3H_7$ |
| II.a.5 | 1 | (2)-$OCH_3$ | —$CH_2$—O—$CH_3$ |
| II.a.6 | 1 | (2)-$OCH_3$ | —$OCH_3$ |
| II.a.7 | 1 | (2)-$OCH_3$ | —$OC_2H_5$ |
| II.a.8 | 1 | (2)-$OCH_3$ | —O-iso-$C_3H_7$ |
| II.a.9 | 1 | (2)-$OCH_3$ | —$SCH_3$ |
| II.a.10 | 1 | (2)-$OCH_3$ | —$SC_2H_5$ |
| II.a.11 | 1 | (2)-$OCH_3$ | —S-iso-$C_3H_7$ |
| II.a.12 | 1 | (2)-$OCH_3$ | —$NHCH_3$ |
| II.a.13 | 1 | (2)-$OCH_3$ | —$NHC_2H_5$ |
| II.a.14 | 1 | (2)-$OCH_3$ | —NH-iso-$C_3H_7$ |
| II.a.15 | 1 | (2)-$OCH_3$ | —N($CH_3$)$_2$ |
| II.a.16 | 1 | (2)-$OCH_3$ | —NH—$C_3H_5$ |
| II.a.17 | 1 | (2)-$OCH_3$ | —$C_3H_5$ |
| II.a.18 | 2 | (2)-$OCH_3$(5)-$CH_3$ | —$CH_3$ |
| II.a.19 | 2 | (2)-$OCH_3$(5)-$CH_3$ | —$C_2H_5$ |
| II.a.20 | 2 | (2)-$OCH_3$(5)-$CH_3$ | -n-$C_3H_7$ |
| II.a.21 | 2 | (2)-$OCH_3$(5)-$CH_3$ | -iso-$C_3H_7$ |
| II.a.22 | 2 | (2)-$OCH_3$(5)-$CH_3$ | —$CH_2$—O—$CH_3$ |
| II.a.23 | 2 | (2)-$OCH_3$(5)-$CH_3$ | —$OCH_3$ |
| II.a.24 | 2 | (2)-$OCH_3$(5)-$CH_3$ | —$OC_2H_5$ |
| II.a.25 | 2 | (2)-$OCH_3$(5)-$CH_3$ | —O-iso-$C_3H_7$ |

TABLE B-continued

| No. | n | R⁷ | R¹¹ |
|---|---|---|---|
| II.a.26 | 2 | (2)-OCH$_3$(5)-CH$_3$ | —SCH$_3$ |
| II.a.27 | 2 | (2)-OCH$_3$(5)-CH$_3$ | —SC$_2$H$_5$ |
| II.a.28 | 2 | (2)-OCH$_3$(5)-CH$_3$ | —S-iso-C$_3$H$_7$ |
| II.a.29 | 2 | (2)-OCH$_3$(5)-CH$_3$ | —NHCH$_3$ |
| II.a.30 | 2 | (2)-OCH$_3$(5)-CH$_3$ | —NHC$_2$H$_5$ |
| II.a.31 | 2 | (2)-OCH$_3$(5)-CH$_3$ | —NH-iso-C$_3$H$_7$ |
| II.a.32 | 2 | (2)-OCH$_3$(5)-CH$_3$ | —N(CH$_3$)$_2$ |
| II.a.33 | 2 | (2)-OCH$_3$(5)-CH$_3$ | —C$_3$H$_5$ |
| II.a.34 | 2 | (2)-OCH$_3$(5)-CH$_3$ | —NH—C$_3$H$_5$ |

An especially preferred safener of the formula II which, as component B, is part of the composition according to the invention is the safener of formula II.a.12 as defined above:

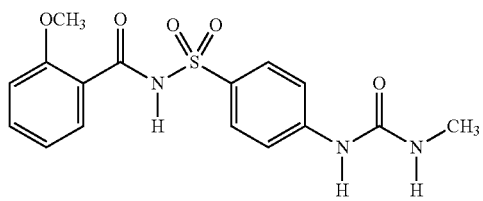

II.a.12

The safeners of formula II can be prepared by standard processes of organic chemistry, for example as described in EP 365 484.

The benzoxazinones of formula I according to the invention can be prepared by standard processes of organic chemistry, for example by the following processes:

Process A)

In analogy to J. Chem. Soc. Perkin Trans. (1982), p. 1321:

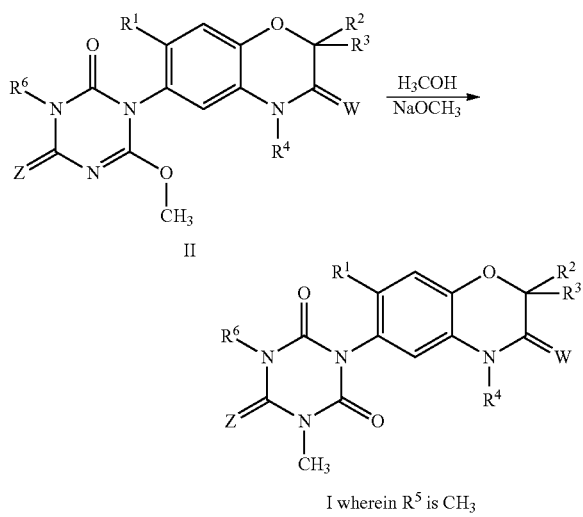

The reaction is conducted as specified in the publication stated.

Process B)

Reaction of isocyanate compounds IV.d with ureas III, followed by cyclization of the urea compounds IV.e:

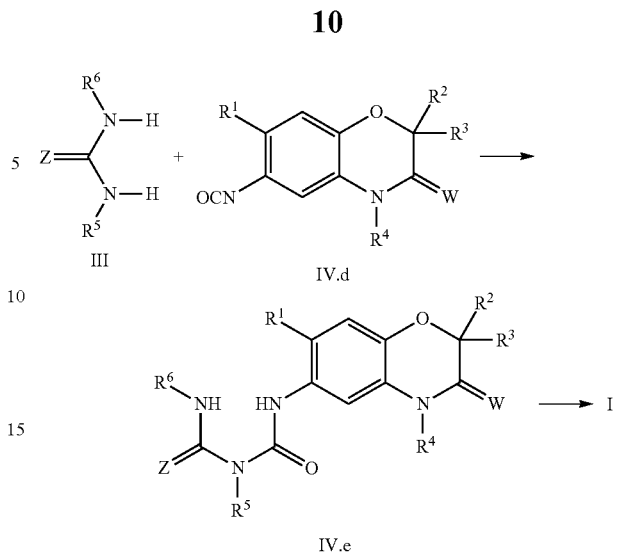

The isocyanate compounds IV.d are reacted with the ureas III. The cyclization of the urea compounds IV.e is carried out in the presence of an activated carbonyl source such as carbonyldiimidazole, phosgene, diphosgene, triphosgene and chloroformic ester, preferably without isolation of the intermediate IV.e.

The reaction of the urea III with the isocyanate compound IV.d as well as the subsequent cyclization of the urea compounds IV.e are usually carried out at from −20° C. to the boiling point of the reaction mixture, preferably at from 20° C. to 200° C., particularly preferably at from 50° C. to 120° C., in an inert organic solvent in the presence of a base and, if appropriate, a catalyst [I. Wakeshima et. al., Bull. Chem. Soc. 1975, 48 (3), 1069-70].

Suitable solvents are aliphatic hydrocarbons such as pentane, hexane, cyclohexane and mixtures of C$_5$-C$_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, nitriles such as acetonitrile and propionitrile, ketones such as acetone, methyl ethyl ketone, diethyl ketone and tert-butyl methyl ketone, as well as dimethylsulfoxide, dimethylformamide and N,N-dimethylacetamide or N-methylpyrrolidone. Particular preference is given to aromatic hydrocarbons such as toluene, o-, m- and p-xylene.

It is also possible to use mixtures of the solvents mentioned.

Suitable bases are, in general inorganic compounds such as alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as triethylamine.

The bases are generally employed in catalytic amounts, however they can also be employed in equimolar amounts, in excess or, if appropriate, be used as solvent.

As acidic catalysts Lewis acids like boron trifluoride, aluminium chloride, ferric-III-chloride, tin-IV-chloride, titanium-IV-chloride and zinc-II-chloride, can be used.

The acids are generally employed in catalytic amounts, however they can also be employed in equimolar amounts, in excess or, if appropriate, be used as solvent.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature. If the intermediates and the end products are obtained as solid, purification can also be carried out by recrystallisation or digestion.

The isocyanate compounds IV.d in turn can be obtained from the corresponding amine compounds IV.c:

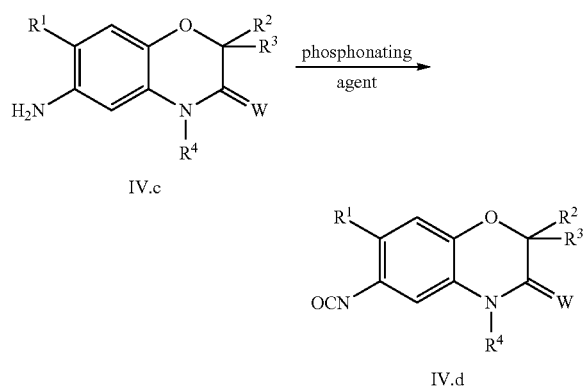

Suitable phosgenating agents are phosgene, diphosgene or triphosgene, diphosgene being preferred.

The reaction of the amine IV.c is usually carried out at from −20° C. to the boiling point of the reaction mixture, preferably at from 10° C. to 200° C., particularly preferably at from 20° C. to 150° C., in an inert organic solvent and, if appropriate, in the presence of a base.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to aromatic hydrocarbons such as toluene, o-, m- and p-xylene.

It is also possible to use mixtures of the solvents mentioned.

Suitable bases are, in general inorganic compounds such as alkali metal and alkaline earth metal carbonates such as lithium carbonate, potassium carbonate and calcium carbonate, as well as alkali metal bicarbonates such as sodium bicarbonate, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as triethylamine.

The bases are generally employed in catalytic amounts, however they can also be employed in equimolar amounts, in excess or, if appropriate, be used as solvent.

Work up can be carried out in a known manner.

The amino compounds IV.c in turn can be obtained from the corresponding nitro compounds IV.b:

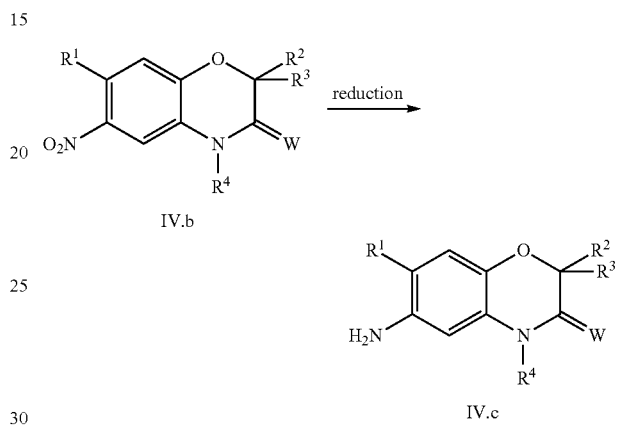

The reduction of the nitro compounds IV.b is usually carried out at from 20° C. to the boiling point of the reaction mixture, preferably at from 20° C. to 200° C., particularly preferably at from 20° C. to 100° C., in an inert organic solvent [Organikum, Heidelberg, 1993, pages 320-323].

Suitable reducing agents are nascent $H_2$; hydrogen in the presence of catalytic amounts of transition metals or transition metal compounds, in particular those of the 8th transition group, preferably Ni, Pd, Pt, Ru or Rh, either as such, in supported form e.g. supported via activated carbon, Al, $ZrO_2$, $TiO_2$, $SiO_2$, carbonates and the like, or in compounds such as palladium oxide or platinum oxide; or metal hydrides, semimetal hydrides such as aluminium hydride and hydrides derived therefrom such as lithium aluminium hydride, diisobutylaluminiumhydride, borohydrides such as diborane or boranates derived therefrom such as sodium borohydride or lithium borohydride.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, alcohols such as methanol, ethanol, n-propanol, isopropanol, n-butanol and tert.-butanol. Particular preference is given to toluene and methanol. It is also possible to use mixtures of the solvents mentioned.

Work up can be carried out in a known manner.

The nitro compounds IV.b in turn can be obtained from the corresponding phenyl compounds IVa:

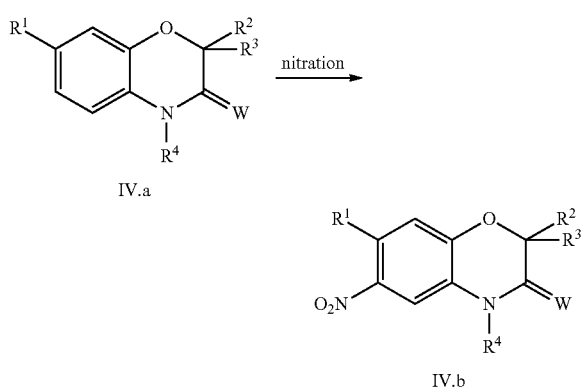

IV.a

IV.b

The nitration of the phenyl compound IV.a is usually carried out at from −20° C. to 100° C., particularly preferably at from 0° C. to 20° C. [Organikum, Heidelberg, 1993, pages 553-557]. Suitable nitrating agents are mixtures of $H_2SO_{4\,conc}$ and $HNO_{3\,conc}$, preferably in a range of 50:1 to 1:50, more preferably 20:1 to 1:20, especially preferred in a range of 10:1 to 1:10.

Work up can be carried out in a known manner.

Those nitro compounds IV.b, wherein $R^4$ is $C_3$-$C_6$-alkenyl, $C_3$-$C_6$-haloalkenyl, $C_3$-$C_6$-alkynyl or $C_3$-$C_6$-haloalkynyl, preferably $C_3$-$C_6$-alkynyl, can also be prepared by alkylation of nitro compounds IV.b, wherein $R^4$ is H:

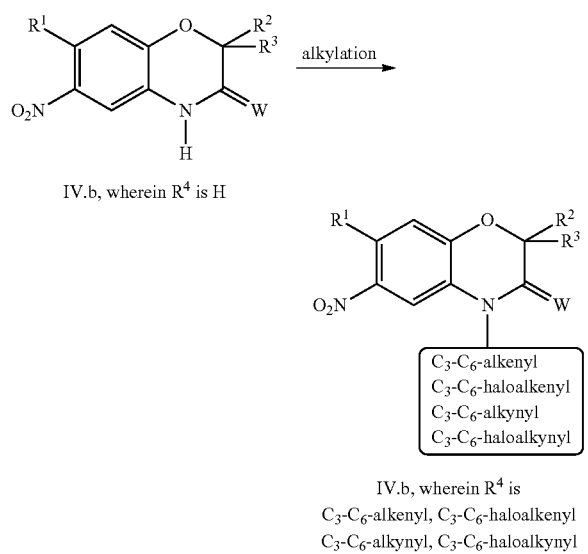

IV.b, wherein $R^4$ is H

IV.b, wherein $R^4$ is
$C_3$-$C_6$-alkenyl, $C_3$-$C_6$-haloalkenyl
$C_3$-$C_6$-alkynyl, $C_3$-$C_6$-haloalkynyl This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide.

Particular preference is given to ethers such as diethyl ether, diisopropyl ether, tert.-butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to tertiary amines such as trimethylamine, triethylamine, diisopropylethylamine and alkali metal and alkaline earth metal alkoxides such as sodium methoxide, sodium ethoxide, potassium ethoxide. The bases are generally employed in catalytic amounts, however they can also be employed in equimolar amounts, in excess or, if appropriate, be used as solvent.

Work up can be carried out in a known manner.

The phenyl compounds IV.a in turn can be obtained from the corresponding acetamides V:

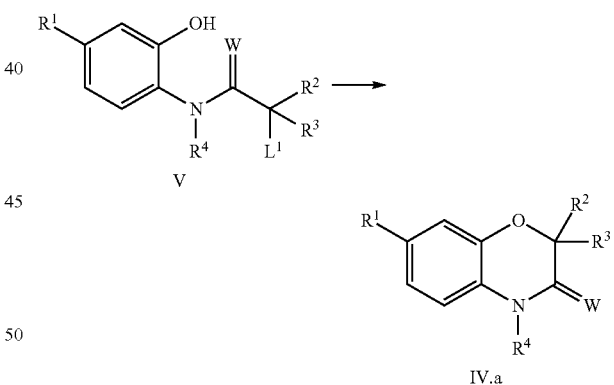

V

IV.a

The cyclisation of the acetamide V is usually carried out at from 0° C. to the boiling point of the reaction mixture, preferably at from 0° C. to 140° C., particularly preferably at from 20° C. to 120° C., in an inert organic solvent in the presence of a base [WO 02/066471].

$L^1$ is halogen selected from Cl, Br, I; preferably Cl or Br; most preferably Cl, also most preferably Br.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, as well as dimethylsulfoxide.

It is also possible to use mixtures of the solvents mentioned.

Suitable bases are, in general inorganic compounds such as alkali metal and alkaline earth metal hydroxides such as lithium hydroxide, sodium hydroxide, potassium hydroxide and calcium hydroxide, alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to 1,8-Diazabicyclo[5.4.0]undec-7-en (DBU). The bases are generally employed in catalytic amounts, however they can also be employed in equimolar amounts, in excess or, if appropriate, be used as solvent.

Work up can be carried out in a known manner.

The acetamides V in turn can be obtained from the corresponding phenol VI:

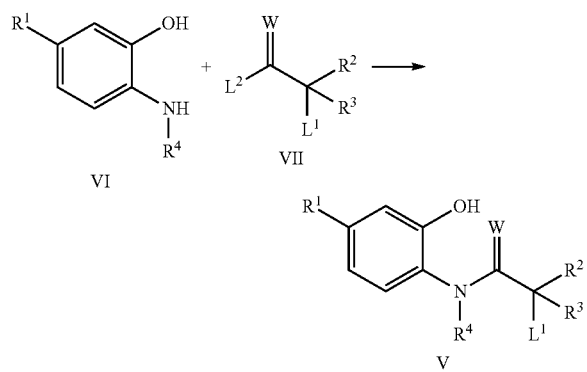

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

$L^1$ is halogen selected from Cl, Br, I; preferably Cl or Br; most preferably Cl, also most preferably Br.

$L^2$ is a known activating group for acylations, e.g. halogen or $C_1$-$C_6$-alkoxy, preferably Cl or $C_1$-$C_6$-alkoxy, most preferably Cl, $OCH_3$ or $OC_2H_5$.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide.

Particular preference is given to ethers such as diethyl ether, diisopropyl ether, tert.-butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as trimethylamine, triethylamine, diisopropylethylamine and alkali metal and alkaline earth metal alkoxides such as sodium methoxide, sodium ethoxide, potassium ethoxide. The bases are generally employed in catalytic amounts, however they can also be employed in equimolar amounts, in excess or, if appropriate, be used as solvent.

Work up can be carried out in a known manner.

The phenols VI required for the preparation of the acetamides V are known from the literature [WO 02/066471] or they can be prepared in accordance with the literature cited and/or are commercially available.

The compounds VII required for the preparation of the acetamides V are commercially available.

Process C)

Alkylation of the benzoxazinones of formula I, where $R^4$ is hydrogen, in a manner known per se (e.g. see also above for the nitro compounds IV.b) leads to benzoxazinones of formula I, wherein $R^4$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl or $C_3$-$C_6$-cycloalkyl-$C_1$-$C_6$-alkyl. The alkylation is carried out in a manner known per se, for example, using an alkylating reagent, e.g. a halide $R^4$-Hal, in the presence of a base, in a solvent.

Processes A) and C) are preferably carried out in the presence of a suitable reaction auxiliary.

Suitable reactants are, in general, the customary inorganic or organic bases and acid acceptors. These preferably include the acetates, amides, carbonates, hydrogencarbonates, hydrides, hydroxides and alkoxides of alkali metals and alkaline earth metals, i.e., for example, sodium acetate, potassium acetate, calcium acetate, lithium amide, sodium amide, potassium amide, calcium amide, sodium carbonate, potassium carbonate, calcium carbonate, sodium hydrogen carbonate, potassium hydrogen carbonate, calcium hydrogen carbonate, lithium hydride, sodium hydride, potassium hydride, calcium hydride, lithium hydroxide, sodium hydroxide, potassium hydroxide, calcium hydroxide, sodium methoxide, sodium ethoxide, sodium n-propoxide, sodium isopropoxide, sodium n-butoxide, sodium isobutoxide, sodium sec-butoxide, sodium tert-butoxide, potassium methoxide, potassium ethoxide, potassium n-propoxide, potassium isopropoxide, potassium n-butoxide, potassium isobutoxide, potassium sec-butoxide, potassium tert-butoxide; furthermore also basic organic nitrogen compounds, for example trimethylamine, triethylamine, tripropylamine, tributylamine, ethyldiisopropylamine, N,N-dimethylcyclohexylamine, dicyclohexylamine, ethyldiisopropylamine, N,N-dimethylaniline, N,N-dimethylbenzylamine, pyridine, 2-methylpyridine, 3-methylpyridine, 4-methylpyridine, 2,4-dimethylpyridine, 2,6-dimethylpyridine, 3,4-dimethylpyridine and 3,5-dimethylpyridine, 5-ethyl-2-methylpyridine, 4-dimethylaminopyridine, N-methylpiperidine, 1,4-diazabicyclo[2,2,2]octane (DABCO), 1,5-diazabicyclo[4,3,0]non-5-ene (DBN) or 1,8-diazabicyclo[5,4,0]undec-7-ene (DBU).

Processes A) and C) are usually carried out in the presence of an inert diluent, suitable diluents generally being the usual organic solvents. These preferably include aliphatic, alicyclic and aromatic, optionally halogenated hydrocarbons, for example pentane, hexane, heptane, petroleum ether, ligroin, benzene, toluene, the xylenes, chlorobenzenes, dichlorobenzenes, cyclohexane, methylcyclohexane, dichloromethane, trichloromethane, tetrachloromethane, dialkyl ethers such as diethyl ether, diisopropyl ether, methyl tert-butyl ether (MTBE), ethyl tert-butyl ether, methyl tert-pentyl ether (TAME), ethyl tert-pentyl ether, tetrahydrofuran, 1,4-dioxane, ethylene glycol dimethyl ether, ethylene glycol diethyl ether, diethylene glycol dimethyl ether, diethylene glycol diethyl ether; dialkyl ketones such as acetone, butanone (methyl ethyl ketone), methyl isopropyl ketone and methyl isobutyl ketone; nitriles such as acetonitrile, propionitrile, butyronitrile and benzonitrile; amides such as N,N-dimethylformamide, N,N-dimethylacetamide, N-methylformanilide, N-methylpyrrolidone and hexamethylphosphoric triamide; esters such as methyl acetate, ethyl acetate, n-propyl acetate, isopropyl acetate, n-butyl acetate, isobutyl acetate and sec-butyl acetate; sulfoxides such as dimethyl sulfoxide; alkanols such as methanol, ethanol, n-propanol, isopropanol, n-butanol, isobutanol, sec-butanol and tert-butanol; glycol ethers such as ethylene glycol monomethyl ether, ethylene glycol monoethyl ether, diethylene glycol monomethyl ether and diethylene glycol monoethyl ether; their mixtures with water, or pure water.

When carrying out processes A) and C), the reaction temperatures can be varied within a substantial range, such as from 0 to 200° C. The processes are preferably carried out at from 10 to 150° C., in particular at from 20° C. to the boiling point of the reaction mixture in question.

In general, the starting materials are employed in approximately equimolar amounts. However, it is also possible to use an excess of each of the reactants, up to approximately twice the molar amount of the other reactant.

Processes A) and C) are expediently carried out under atmospheric pressure or under the inherent pressure of the reaction mixture in question. However, the processes may also be carried out under elevated or reduced pressure, in general at from 0.1 to 10 bar.

As a rule, the reaction mixtures in question are worked up by methods known per se, for example by diluting the reaction solution with water and subsequently isolating the product by means of filtration, crystallization or solvent extraction, or by removing the solvent, partitioning the residue in a mixture of water and a suitable organic solvent, and working up the organic phase to give the product.

The compositions comprising a benzoxazinone of the general formula I, a safener of formula II and optionally one or more further herbicide(s) C are suitable as herbicides. They are suitable as such or as an appropriately formulated composition comprising a benzoxazinone of the general formula I, a safener of formula II and optionally one or more further herbicide(s) C.

They act against broad-leaved weeds and grass weeds in crops such as wheat, rice, maize, soya and cotton without causing any significant damage to the crop plants. This effect is mainly observed at low rates of application.

Depending on the application method in question, the compositions comprising a benzoxazinone of the general formula I, a safener of formula II and optionally a further herbicide C can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera, Zea mays* and turf grass species.

Preferred crops are the following: *Arachis hypogaea, Avena sativa, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera, Zea mays* and turf grass species.

More preferred crops are crops of cereals, corn, soybeans, rice, oilseed rape, cotton, potatoes, peanuts, turf grass species or permanent crops.

Especially preferred crops are *Avena sativa, Hordeum vulgare, Secale cereale, Triticale, Triticum aestivum, Triticum durum, Zea mays, Sorghum bicolor* (*s. vulgare*), *Saccharum officinarum,* turf grass species and permanent crops, soybeans and *Orysa sativa.*

The compositions comprising a benzoxazinone of the general formula I, a safener of formula II and optionally one or more further herbicide(s) C according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetylCoA carboxylase (AC-Case) inhibitors; or oxynil (i.e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or AC-Case inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutgenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as deltaendotoxins, e.g., CryIA(b), CryIA(c), CryIF, CryIF(a2), CryIIA(b), CryIIIA, CryIIIB(b1) or Cry9c; vegetative insecticidal proteins (VIP), e.g., VIP1, VIP2, VIP3 or VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, or other insect-specific neurotoxins; toxins produced by fungi, such as *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pretoxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e.g., oil crops that produce health-promoting long-chain omega-3 fatty acids or unsaturated omega-9 fatty acids (e.g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The compositions comprising a benzoxazinone of the general formula I, a safener of formula II and optionally one or more further herbicide(s) C according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding.

Suitable are for example crop plants, preferably corn, wheat, sunflower, sugarcane, cotton, rice, canola, oilseed rape or soybeans, which crops are resistant to herbicidal PPO inhibitors, or crop plants which, owing to introduction of the gene for Bt toxin by genetic modification, are resistant to attack by certain insects.

The compositions comprising a benzoxazinone of the general formula I, a safener of formula II and optionally one or more further herbicide(s) C, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The formulated compositions comprise a benzoxazinone of the general formula I, a safener of formula II, optionally one or more further herbicide(s) C, and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formutations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhard).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water.

To prepare emulsions, pastes or oil dispersions, the benzoxazinones of the formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the active compounds, especially of the benzoxazinone of the formula I and the safener of formula II, in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the active compounds, especially of the benzoxazinone of the formula I and the safener of formula II according to the present invention the active ingredients are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The active compounds, especially of the benzoxazinone of the formula I and the safener of formula II according to the present invention can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The active compounds according to the present invention, especially of the benzoxazinone of the formula I and the safener of formula II, can be applied pre-, post-emergence or pre-plant, or together with the seed of a crop plant. It is also possible to apply the formulated composition or active compounds by applying seed, pretreated with the formulated compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the active compounds according to the present invention, especially of the benzoxazinone of the formula I and the safener of formula II, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the active compounds according to the present invention, especially on the benzoxazinone of the formula I and safener of formula II or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The rates of application of the benzoxazinone of formula I according to the present invention (total amount of benzoxazinone I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the benzoxazinones of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the benzoxazinones of formula I is 0.1 to 1000 g/ha, preferably 1 to 750 g/ha, more preferably 5 to 500 g/ha, of active substance.

To treat the seed, the benzoxazinones I are generally employed in amounts of from 0.001 to 10 kg per 100 kg of seed.

The rates of application of the safener of formula II according to the present invention (total amount of safener II) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the safener II are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the safener II is 0.1 to 1000 g/ha, preferably 1 to 750 g/ha, more preferably 5 to 500 g/ha, of active substance.

To treat the seed, the safener II are generally employed in amounts of from 0.001 to 10 kg per 100 kg of seed.

To broaden the spectrum of action and to achieve synergistic effects, the active compounds according to the present invention, the benzoxazinone of the formula I and the safener of formula II, may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may furthermore be beneficial to apply the active compounds according to the present invention alone or in combination with other herbicides C, or else in the form of a mixture with other crop protection agents, for example together with agents for controlling pests or phytopathogenic fungi or bacteria.

Also of interest is the miscibility with mineral salt solutions, which are employed for treating nutritional and trace element deficiencies. Other additives such as non-phytotoxic oils and oil concentrates may also be added.

The further active compound C (herbicide C) is preferably selected from the herbicides of class c1) to c15):
- c1) lipid biosynthesis inhibitors;
- c2) acetolactate synthase inhibitors (ALS inhibitors);
- c3) photosynthesis inhibitors;
- c4) protoporphyrinogen-IX oxidase inhibitors,
- c5) bleacher herbicides;
- c6) enolpyruvyl shikimate 3-phosphate synthase inhibitors (EPSP inhibitors);
- c7) glutamine synthetase inhibitors;
- c8) 7,8-dihydropteroate synthase inhibitors (DHP inhibitors);
- c9) mitosis inhibitors;
- c10) inhibitors of the synthesis of very long chain fatty acids (VLCFA inhibitors);
- c11) cellulose biosynthesis inhibitors;
- c12) decoupler herbicides;
- c13) auxinic herbicides;
- c14) auxin transport inhibitors; and
- c15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenolbutyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

In one embodiment of the present invention the compositions according to the present invention comprise at least one benzoxazinone of formula I (compound A), at least one safener of the formula II, and at least one further active compound selected from herbicides C, preferably herbicides C of class c1) to c15).

Preference is given to those compositions according to the present invention comprising at least one herbicide C selected from herbicides of class c1, c2, c3, c4, c5, c6, c7, c9, c10 and c13.

Specific preference is given to those compositions according to the present invention which comprise at least one herbicide C selected from the herbicides of class c3, c4, c6, c9 and c10.

Particular preference is given to those compositions according to the present invention which comprise at least one herbicide C selected from the herbicides of class c4, c6, c9 and c10.

According to one embodiment of the invention the composition contains as optional herbicide C at least one inhibitor of the lipid biosynthesis (herbicide c1). These are compounds that inhibit lipid biosynthesis. Inhibition of the lipid biosynthesis can be affected either through inhibition of acetylCoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to another embodiment of the invention the composition contains as optional herbicide C at least one ALS inhibitor (herbicide c2). The herbicidal activity of these compounds is based on the inhibition of acetolactate synthase and thus on the inhibition of the branched chain amino acid biosynthesis. These inhibitors belong to the group B of the HRAC classification system.

According to another embodiment of the invention the composition contains as optional herbicide C at least one inhibitor of photosynthesis (herbicide c3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to another embodiment of the invention the composition contains as optional herbicide C at least one inhibitor of protoporphyrinogen-IX-oxidase (herbicide c4). The herbicidal activity of these compounds is based on the inhibition of the protoporphyrinogen-IX-oxidase. These inhibitors belong to the group E of the HRAC classification system.

According to another embodiment of the invention the composition contains as optional herbicide C at least one bleacher-herbicide (herbicide c5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenylpyruvate-dioxygenase (HPPD inhibitors, group F2 of HRAC classification), compounds that inhibit DOXsynthase (group F4 of HRAC class) and compounds which inhibit carotenoid biosynthesis by an unknown mode of action (bleacher—unknown target, group F3 of HRAC classification).

According to another embodiment of the invention the composition contains as optional herbicide C at least one EPSP synthase inhibitor (herbicide c6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

According to another embodiment of the invention the composition contains as optional herbicide C at least one glutamine synthetase inhibitor (herbicide c7). The herbicidal activity of these compounds is based on the inhibition of glutamine synthetase, and thus on the inhibition of the aminoacid biosynthesis in plants. These inhibitors belong to the group H of the HRAC classification system.

According to another embodiment of the invention the composition contains as optional herbicide C at least one DHP synthase inhibitor (herbicide c8). The herbicidal activity of these compounds is based on the inhibition of 7,8-dihydropteroate synthase. These inhibitors belong to the group I of the HRAC classification system.

According to another embodiment of the invention the composition contains as optional herbicide C at least one mitosis inhibitor (herbicide c9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

According to another embodiment of the invention the composition contains as optional herbicide C at least one VLCFA inhibitor (herbicide c10). The herbicidal activity of these compounds is based on the inhibition of the synthesis of very long chain fatty acids and thus on the disturbance or inhibition of cell division in plants. These inhibitors belong to the group K3 of the HRAC classification system.

According to another embodiment of the invention the composition contains as optional herbicide C at least one cellulose biosynthesis inhibitor (herbicide c11). The herbicidal activity of these compounds is based on the inhibition of the biosynthesis of cellulose and thus on the inhibition of the synthesis of cell walls in plants. These inhibitors belong to the group L of the HRAC classification system.

According to another embodiment of the invention the composition contains as optional herbicide C at least one decoupler herbicide (herbicide c12). The herbicidal activity of these compounds is based on the disruption of the cell membrane. These inhibitors belong to the group M of the HRAC classification system.

According to another embodiment of the invention the composition contains as optional herbicide C at least one auxinic herbicide (herbicide c13). These include compounds that mimic auxins, i.e. plant hormones, and affect the growth of the plants. These compounds belong to the group O of the HRAC classification system.

According to another embodiment of the invention the composition contains as optional herbicide C contain at least one auxin transport inhibitor (herbicide c14). The herbicidal activity of these compounds is based on the inhibition of the auxin transport in plants. These compounds belong to the group P of the HRAC classification system. As to the given mechanisms of action and classification of the active substances, see e.g. "HRAC, Classification of Herbicides According to Mode of Action", http://www.plantprotection.org/hrac/MOA.html.

Examples of herbicides C which can be used in combination with the compositions comprising a benzoxazinone of formula I and a safener of formula II according to the present invention are:

c1) from the group of the lipid biosynthesis inhibitors: ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofoptefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

c2) from the group of the ALS inhibitors: sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone. Among these, a preferred embodiment of the invention relates to those compositions comprising at least one imidazolinone herbicide;

c3) from the group of the photosynthesis inhibitors: amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

c4) from the group of the protoporphyrinogen-IX oxidase inhibitors: acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

c5) from the group of the bleacher herbicides: PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

c6) from the group of the EPSP synthase inhibitors: glyphosate, glyphosate-isopropylammonium, glyposate-potassium and glyphosate-trimesium (sulfosate);

c7) from the group of the glutamine synthase inhibitors: bilanaphos (bialaphos), bilanaphos-sodium, glufosinate, glufosinate-P and glufosinate-ammonium;

c8) from the group of the DHP synthase inhibitors: asulam;

c9) from the group of the mitosis inhibitors: compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophosmethyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

c10) from the group of the VLCFA inhibitors: chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napropanilide and napropamide, tetrazolinones such fentrazamide, and other herbicides such as anilofos, cafenstrole, fenoxasulfone, ipfencarbazone, piperophos, pyroxasulfone and isoxazoline compounds of the formula II,

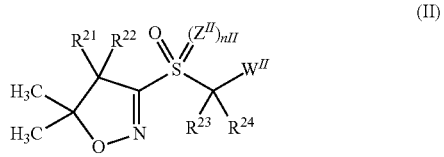

(II)

wherein $R^{21}$, $R^{22}$, $R^{23}$, $R^{24}$, W, Z and n have the following meanings:

$R^{21}$, $R^{22}$, $R^{23}$, $R^{24}$ independently of one another hydrogen, halogen or $C_1$-$C_4$-alkyl;

$W^{II}$ phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;

preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$;

$Z^{II}$ oxygen or NH; and $n^{II}$ zero or one;

among the isoxazoline compounds of the formula II, preference is given to isoxazoline compounds of the formula II, wherein $R^{21}$, $R^{22}$, $R^{23}$, $R^{24}$ independently of one another are H, F, Cl or methyl;

$Z^{II}$ is oxygen;

$n^{II}$ is 0 or 1; and $W^{II}$ is phenyl, pyrazolyl or 1,2,3-triazolyl, wherein the three last-mentioned radicals are unsubstituted or carry one, two or three substituents $R^{yy}$, especially one of the following radicals

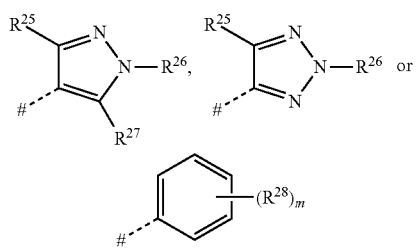

wherein $R^{25}$ is halogen, $C_1$-$C_4$-alkyl or $C_1$-$C_4$-haloalkyl;

$R^{26}$ is $C_1$-$C_4$-alkyl;

$R^{27}$ is halogen, $C_1$-$C_4$-alkoxy or $C_1$-$C_4$-haloalkoxy;

$R^{28}$ is halogen, $C_1$-$C_4$-alkyl, $C_1$-$C_4$-haloalkyl or $C_1$-$C_4$-haloalkoxy;

m is 0, 1, 2 or 3; and # denotes the point of attachment to the group $CR^{23}R^{24}$;

among the isoxazoline compounds of the formula II, particular preference is given to those isoxazoline compounds of the formula II, wherein $R^{21}$ is hydrogen;

$R^{22}$ is fluorine;

$R^{23}$ is hydrogen or fluorine;

$R^{24}$ is hydrogen or fluorine;

$W^{II}$ is one of the radicals of the formulae $W^1$, $W^2$, $W^3$ or $W^4$

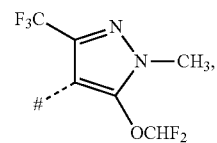

$W^1$

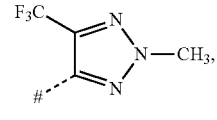

$W^2$

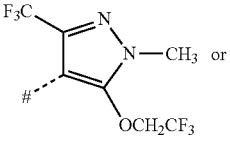

$W^3$

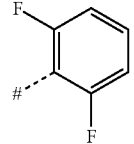

$W^4$ wherein # denotes the point of attachment to the group $CR^{23}R^{24}$;

$Z^{II}$ is oxygen;

$n^{II}$ is zero or 1, in particular 1; and among these, especially preferred are the isoxazoline compounds of the formulae II.1, II.2, II.3, II.4, II.5, II.6, II.7, II.8 and II.9

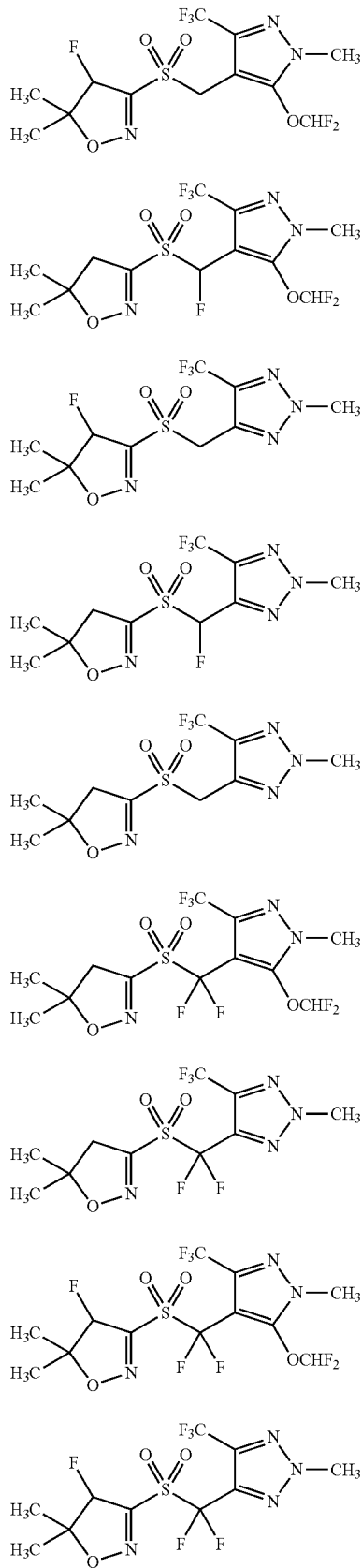

the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxya-cetamides;

c11) from the group of the cellulose biosynthesis inhibitors: chlorthiamid, dichlobenil, flupoxam, isoxaben, 1-Cyclohexyl-5-pentafluorphenyloxy-1$^4$-[1,2,4,6]thiatriazin-3-ylamine and piperazine compounds of formula III,

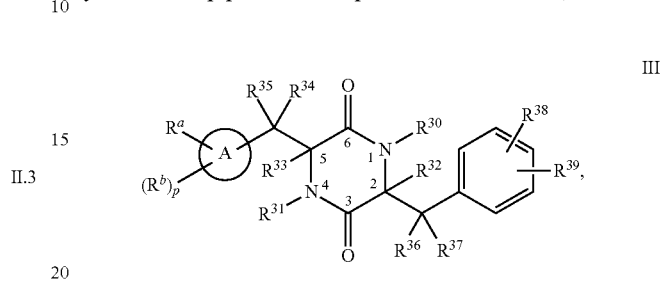

in which

A is phenyl or pyridyl where $R^a$ is attached in the ortho-position to the point of attachment of A to a carbon atom;

$R^a$ is CN, NO$_2$, D-C$_3$-C$_6$-cycloalkyl, C$_1$-C$_4$-alkoxy, C$_1$-C$_4$-haloalkoxy, O-D-C$_3$-C$_6$-cycloalkyl, S(O)$_q$R$^y$, C$_2$-C$_6$-alkenyl, D-C$_3$-C$_6$-cycloalkenyl, C$_3$-C$_6$-alkenyloxy, C$_2$-C$_6$-alkynyl, C$_3$-C$_6$-alkynyloxy, NR$^A$R$^B$, tri-C$_1$-C$_4$-alkylsilyl, D-C(=O)—R$^{a1}$, D-P(=O)(R$^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups R$^{aa}$ and/or R$^{a1}$, and, if R$^a$ is attached to a carbon atom, additionally halogen;

$R^y$ is C$_1$-C$_6$-alkyl, C$_3$-C$_4$-alkenyl, C$_3$-C$_4$-alkynyl, NR$^A$R$^B$ or C$_1$-C$_4$-haloalkyl and q is 0, 1 or 2;

$R^A$, $R^B$ independently of one another are hydrogen, C$_1$-C$_6$-alkyl, C$_3$-C$_6$-alkenyl and C$_3$-C$_6$-alkynyl; together with the nitrogen atom to which they are attached, R$^A$, R$^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups R$^{aa}$;

D is a covalent bond, C$_1$-C$_4$-alkylene, C$_2$-C$_6$-alkenyl or C$_2$-C$_6$-alkynyl;

$R^{a1}$ is hydrogen, OH, C$_1$-C$_8$-Alkyl, C$_1$-C$_4$-haloalkyl, C$_3$-C$_6$-cycloalkyl, C$_2$-C$_8$-alkenyl, C$_5$-C$_6$-cycloalkenyl, C$_2$-C$_8$-alkynyl, C$_1$-C$_6$-alkoxy, C$_1$-C$_4$-haloalkoxy, C$_3$-C$_8$-alkenyloxy, C$_3$-C$_8$-alkynyloxy, NR$^A$R$^B$, C$_1$-C$_6$-alkoxyamino, C$_1$-C$_6$-alkylsulfonylamino, C$_1$-C$_6$-alkylaminosulfonylamino, [di-(C$_1$-C$_6$)alkylamino]sulfonylamino, C$_3$-C$_6$-alkenylamino, C$_3$-C$_6$-alkynylamino, N—(C$_2$-C$_6$-alkenyl)-N—(C$_1$-C$_6$-alkyl)amino, N—(C$_2$-C$_6$-alkynyl)-N—(C$_1$-C$_6$-alkyl)amino, N—(C$_1$-C$_6$-alkoxy)-N—(C$_1$-C$_6$-alkyl) amino, N—(C$_2$-C$_6$-alkenyl)-N—(C$_1$-C$_6$-alkoxy) amino, N—(C$_2$-C$_6$-alkynyl)-N—(C$_1$-C$_6$-alkoxy)-amino, C$_1$-C$_6$-alkylsulfonyl, tri-C$_1$-C$_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^{aa}$;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another are hydrogen, CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0, 1, 2 or 3;

$R^{30}$ is hydrogen, OH, CN, $C_3$-$C_{12}$-alkenyl, $C_3$-$C_{12}$-alkynyl, alkoxy, $C_3$-$C_6$-cycloalkyl, $C_5$-$C_6$-cycloalkenyl, $NR^A R^B$, $S(O)_n R^y$, $S(O)_n NR^A R^B$, $C(=O)R^{40}$, $CONR^A R^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl, $C_3$-$C_4$-alkynyl, $C_1$-$C_4$-alkoxy, $C_3$-$C_6$-cycloalkyl, $C_5$-$C_6$-cycloalkenyl, $NR^A R^B$, $S(O)_n R_y$, $S(O)_n R^A R^B$, $C(=O)R^{40}$ and $CONR^A R^B$;

$R^{40}$ is hydrogen, $C_1$-$C_4$-alkyl, $C_1$-$C_4$-haloalkyl, $C_1$-$C_4$-alkoxy or $C_1$-$C_4$-haloalkoxy;

$D^1$ is carbonyl or a group D;

where in groups $R^{15}$, $R^a$ and their sub-substituents the carbon chains and/or the cyclic groups may carry 1, 2, 3 or 4 substituents $R^{aa}$ and/or $R^{a1}$;

$R^{31}$ is $C_1$-$C_4$-alkyl, $C_3$-$C_4$-alkenyl or $C_3$-$C_4$-alkynyl;

$R^{32}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or $C(=O)R^{40}$;

$R^{33}$ is hydrogen, halogen, $C_1$-$C_4$-alkyl or $C_1$-$C_4$-haloalkyl, or $R^{33}$ and $R^{34}$ together are a covalent bond;

$R^{34}$, $R^{35}$, $R^{36}$, $R^{37}$ independently of one another are hydrogen, halogen, OH, CN, $NO_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{38}$, $R^{39}$ independently of one another are hydrogen, halogen, OH, haloalkyl, $NR^A R^B$, $NR^A C(O)R^{41}$, CN, $NO_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{41}$, phenoxy or benzyloxy, where in groups $R^{38}$ and $R^{39}$ the carbon chains and/or the cyclic groups may carry 1, 2, 3 or 4 substituents $R^{aa}$;

$R^{41}$ is $C_1$-$C_4$-alkyl or $NR^A R^B$;

among the piperazine compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^A R^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another is CN, $NO_2$, halogen, $C_1$-$C_4$-alkyl, haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{30}$ is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{40}$, which can be partially or fully be substituted by $R^{aa}$ groups;

$R^{40}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{30}$, $R^a$ and their sub-substituents the carbon chains and/or the cyclic groups may carry 1, 2, 3 or 4 substituents $R^{aa}$ and/or $R^{a1}$;

$R^{31}$ is $C_1$-$C_4$-alkyl;

$R^{32}$ is OH, $NH_2$, $C_1$-$C_4$-alkyl, $C_3$-$C_6$-cycloalkyl, $C_1$-$C_4$-haloalkyl or $C(=O)R^{25}$;

$R^{33}$ is hydrogen, or $R^{33}$ and $R^{34}$ together are a covalent bond;

$R^{34}$, $R^{35}$, $R^{36}$, $R^{37}$ independently of one another are hydrogen;

$R^{38}$, $R^{39}$ independently of one another are hydrogen, halogen or OH;

c12) from the group of the decoupler herbicides: dinoseb, dinoterb and DNOC and its salts;

c13) from the group of the auxinic herbicides: 2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

c14) from the group of the auxin transport inhibitors: diflufenzopyr, diflufenzopyr-sodium, naptalam and naptalam-sodium;

c15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Preferred herbicides C that can be used in combination with the compositions comprising a benzoxazinone of formula I and a safener of formula II of the formula I according to the present invention are:

c1) from the group of the lipid biosynthesis inhibitors: clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, benfuresate, dimepiperate, EPTC, esprocarb, ethofumesate, molinate, orbencarb, prosulfocarb, thiobencarb and triallate;

c2) from the group of the ALS inhibitors: amidosulfuron, azimsulfuron, bensulfuronmethyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methylsodium, foramsulfuron, halosulfuron-methyl, imazamethabenz-methyl, imazamox, imazapic, imazapyr, imazaquin, imazethapyr, imazosulfuron, iodosulfuron, iodosulfuronmethyl-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

c3) from the group of the photosynthesis inhibitors: ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

c4) from the group of the protoporphyrinogen-IX oxidase inhibitors: acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

c5) from the group of the bleacher herbicides: aclonifen, beflubutamid, benzobicyclone, clomazone, diflufenican, fluorochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

c6) from the group of the EPSP synthase inhibitors: glyphosate, glyphosate-isopropylammonium, glyphosate-potassium and glyphosate-trimesium (sulfosate);

c7) from the group of the glutamine synthase inhibitors: glufosinate, glufosinate-P, glufosinate-ammonium;

c8) from the group of the DHP synthase inhibitors: asulam;

c9) from the group of the mitosis inhibitors: benfluralin, dithiopyr, ethalfluralin, oryzalin, pendimethalin, thiazopyr and trifluralin;

c10) from the group of the VLCFA inhibitors: acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

c11) from the group of the cellulose biosynthesis inhibitors: dichlobenil, flupoxam, isoxaben, 1-Cyclohexyl-5-pentafluorphenyloxy-1$^4$-[1,2,4,6]thiatriazin-3-ylamine and the piperazine compounds of formula III as mentioned above;

c13) from the group of the auxinic herbicides: 2,4-D and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluoroxypyr-meptyl, MCPA and its salts and esters, MCPB and its salts and esters, mecoprop-P and its salts and esters, picloram and its salts and esters, quinclorac, quinmerac, triclopyr and its salts and esters, and aminocyclopyrachlor and its salts and esters;

c14) from the group of the auxin transport inhibitors: diflufenzopyr and diflufenzopyr-sodium;

c15) from the group of the other herbicides: bromobutide, cinmethylin, cumyluron, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methyl-bromide, MSMA, oxaziclomefone, pyributicarb, triaziflam, tridiphane and 6-chloro-3-(2-cyclopropyl-6-methylphenoxy)-4-pyridazinol (CAS 499223-49-3) and its salts and esters.

Particularly preferred herbicides C that can be used in combination with the compositions comprising a benzoxazinone of formula I and a safener of formula II according to the present invention are:

c1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate;

c2) from the group of the ALS inhibitors: bensulfuronmethyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron;

c3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

c4) from the group of the protoporphyrinogen-IX oxidase inhibitors: flumioxazin, oxyfluorfen, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 2-(2,2,7-Trifluoro-3-oxo-4-prop-2-ynyl-3,4-dihydro-2H-benzo[1,4]oxazin-6-yl)-4,5,6,7-tetrahydroisoindole-1,3-dione, and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

c5) from the group of the bleacher herbicides: benzobicyclone, clomazone, diflufenican, fluorochloridone, isoxaflutole, mesotrione, picolinafen, sulcotrione, tefuryltrione, tembotrione, topramezone, bicyclopyrone, amitrole and flumeturon;

c6) from the group of the EPSP synthase inhibitors: glyphosate, glyphosate-isopropylammonium and glyphosate-trimesium (sulfosate);

c7) from the group of the glutamine synthase inhibitors: glufosinate, glufosinate-P and glufosinate-ammonium;

c9) from the group of the mitosis inhibitors: pendimethalin and trifluralin;

c10) from the group of the VLCFA inhibitors: acetochlor, cafenstrole, dimethenamid-P, fentrazamide, flufenacet, mefenacet, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

c11) from the group of the cellulose biosynthesis inhibitors: isoxaben and the piperazine compounds of formula III as mentioned above;

c13) from the group of the auxinic herbicides: 2,4-D and its salts and esters, aminopyralid and its salts and its esters, clopyralid and its salts and esters, dicamba and its salts and esters, fluoroxypyr-meptyl, quinclorac, quinmerac and aminocyclopyrachlor and its salts and esters;

c14) from the group of the auxin transport inhibitors: diflufenzopyr and diflufenzopyr-sodium, c15) from the group of the other herbicides: dymron (=daimuron), indanofan, indaziflam, oxaziclomefone and triaziflam.

The optional compounds C of groups c1) to c15) are known herbicides, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. The piperazine compounds of formula III as defined above (hereinafter also referred to as "compound III") as well as its pesticidal action and methods for preparation are described in WO 2010/049369, WO 2010/037727 and WO 2010/012649.

The assignment of the active compounds to the respective mechanisms of action is based on current knowledge. If several mechanisms of action apply to one active compound, this substance was only assigned to one mechanism of action.

If the compounds of formula I, the safeners of formula II and the optional herbicides C are capable of forming geometrical isomers, for example E/Z isomers, both the pure isomers and mixtures thereof may be used in the compositions according to the invention.

If the compounds of formula I, the safeners of formula II and the optional herbicides C have one of more centers of chirality and are thus present as enantiomers or diastereomers, both the pure enantiomers and diastereomers and mixtures thereof may be used in the compositions according to the invention.

If the compounds of formula I, the safeners of formula II and the optional herbicides C have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The optional compounds C having a carboxyl group can be employed in the form of the acid, in the form of an agriculturally suitable salt as mentioned above or else in the form of an agriculturally acceptable derivative in the compositions according to the invention, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the methoxyethyl, ethoxyethyl or butoxyethyl ester. An example of a straight-chain or branched $C_1$-$C_{10}$-alkylthio ester is the ethylthio ester.

In the case of dicamba, suitable salts include those, where the counterion is an agriculturally acceptable cation. For example, suitable salts of dicamba are dicambasodium, dicamba-potassium, dicamba-methylammonium, dicamba-dimethylammonium, dicamba-isopropylammonium, dicamba-diglycolamine, dicamba-olamine, dicambadiolamine and dicamba-trolamine. Examples of a suitable ester are dicamba-methyl and dicamba-butoyl.

Suitable salts of 2,4-D are 2,4-D dimethylammonium, 2,4-D diethanolammonium, 2,4-D triethanolammonium, 2,4-D triisopropanolammonium, 2,4-D sodium; 2,4-D isopropylammonium. Examples of a suitable ester of 2,4-D are 2,4-D-butotyl, 2,4-D-butyl, 2,4-Dethyl, 2,4-D-ethylhexyl, 2,4-D-isobutyl, 2,4-D-isoctyl, 2,4-D-isopropyl. Suitable salts of 2,4-DB are for example 2,4-DB sodium, 2,4-DB potassium and 2,4-DB dimethylammonium.

Suitable salts of dichlorprop are for example dichlorprop potassium and dichlorprop dimethylammonium. Examples of a suitable ester of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-methyl, MCPA-olamine, MCPA-potassium, MCPA-sodium and MCPA-trolamine. A suitable salt of MCPB is MCPB sodium. A suitable ester of MCPB is MCPB-ethyl.

Suitable salts of clopyralid are clopyralid potassium, clopyralid olamine and clopyralid triisopropanolammonium.

Examples of a suitable ester of fluoroxypyr are fluoroxypyr-meptyl and fluoroxypyr-2-butoxy-1-methylethyl, wherein fluoroxypyr-meptyl is preferred.

Suitable salts of picloram are picloram dimethylammonium, picloram potassium, picloram triisopropanolammonium, picloram triisopropylammonium and picloram trolamine.

A suitable ester of picloram is picloram-isoctyl.

A suitable salt of triclopyr is triclopyr triethalammonium. A suitable ester of triclopyr is triclopyr-butotyl.

Suitable salts and esters of chloramben include chloramben-ammonium, chlorambendiolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

Suitable salts of glufosinate are for example glufosinate-ammonium and glufosinate-P. Suitable salts and esters of bromoxynil are for example bromoxynil butyrate, bromoxynil heptanoate, bromoxynil octanoate, bromoxynil potassium and bromoxynil sodium;

Suitable salts of ioxonil are for example ioxonil-octanoate, ioxonil-potassium and ioxonil-sodium.

Suitable salts and esters of mecoprop include mecoprop-butotyl, mecopropdimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example butotyl, dimethylammonium, ethylhexyl, potassium and sodium Suitable salts of diflufenzopyr is diflufenzopyr-sodium.

Suitable salts of naptalam is naptalam-sodium.

Suitable salts of DNOC are for example DNOC-ammonium, DNOC-potassium and DNOC-sodium Suitable salts and esters of 2,4-DB are for example 2,4-DB-butylester, 2,4-DB-dimethylammonium, 2,4-DB-triisopropanolammonium, 2,4-DB-isoctyl, 2,4-DB-potassium and 2,4-DB-sodium Suitable salts of aminocyclopyrachlor are for example aminocyclopyrachlor dimethylammonium, aminocyclopyrachlor triisopropanolammonium, aminocyclopyrachlor sodium and aminocyclopyrachlor potassium.

According to a preferred embodiment of the invention, the composition comprises as herbicidal active compound only a benzoxazinone of formula I, preferably exactly one benzoxazinone of formula I, more preferably of formula I.a, especially preferred the benzoxazinone I.a.35, and as safening component only a safener of formula II, preferably exactly one safener of formula II, more preferably a safener of formula II.a, most preferably the safener II.a.12.

According to another preferred embodiment of the invention, the composition comprises, besides a benzoxazinone of formula I, preferably of formula I.a, especially preferred the benzoxazinone I.a.35, and a safener of formula II, more preferably a safener of formula II.a, most preferably the safener II.a.12, at least one additional herbicidal active compound C or component C, preferably exactly one additional herbicide C.

According to another preferred embodiment of the invention, the composition comprises, besides a benzoxazinone of formula I, preferably of formula I.a, especially preferred the benzoxazinone I.a.35, and a safener of formula II, more preferably a safener of formula II.a, most preferably the safener II.a.12, as additional herbicidal active compound C or component C, at least two, preferably exactly two herbicides C different from each other.

According to another preferred embodiment of the invention, the composition comprises, besides a benzoxazinone of formula I, preferably of formula I.a, especially preferred the benzoxazinone I.a.35, and a safener of formula II, more preferably a safener of formula II.a, most preferably the safener II.a.12, as additional herbicidal active compound C or component C, at least three, preferably exactly three additional herbicides C different from each other.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c1), in particular selected from the group consisting of clodinafop-propargyl, cycloxydim, cyhalofopbutyl, fenoxaprop-P-ethyl, pinoxaden, profoxydim, tepraloxydim, tralkoxydim, esprocarb, prosulfocarb, thiobencarb and triallate.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c4), in particular selected from the group consisting of flumioxazin, oxyfluorfen, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c5), in particular selected from the group consisting of clomazone, diflufenican, fluorochloridone, isoxaflutole, mesotrione, picolinafen, sulcotrione, tefuryltrione, tembotrione, topramezone, bicyclopyrone, amitrole and flumeturon.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c6), in particular selected from the group consisting of glyphosate, glyphosate-isopropylammonium and glyphosate-trimesium (sulfosate).

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c7), in particular selected from the group consisting of glufosinate, glufosinate-P and glufosinate-ammonium.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c9), in particular selected from the group consisting of pendimethalin and trifluralin.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c11), in particular isoxaben. Likewise, preference is given to compositions comprising, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group b11) selected from the group consisting of piperazine compounds of formula III as defined above.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c13), in particular selected from the group consisting of 2,4-D and its salts and esters, aminopyralid and its salts such as aminopyralid-tris(2-hydroxypropyl)ammonium and its esters, clopyralid and its salts and esters, dicamba and its salts and esters, fluoroxypyr-meptyl, quinclorac, quinmerac and aminocyclopyrachlor and its salts and esters.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c14), in particular selected from the group consisting of diflufenzopyr and diflufenzopyr-sodium.

According to another preferred embodiment of the invention, the composition comprises, in addition to a benzoxazinone of the formula I, preferably of formula I.a, especially preferred the benzoxazinone I.a.35, and a safener of formula II, more preferably a safener of formula II.a, most preferably the safener II.a.12, at least one and especially exactly one herbicidally active compound from group c15), in particular selected from the group consisting of dymron (=daimuron), indanofan, indaziflam, oxaziclomefone and triaziflam.

Here and below, the term "binary compositions" includes compositions comprising one or more, for example 1, 2 or 3, active compounds of the formula I and one or more, for example 1, 2 or 3, safeners of formula II.

Correspondingly, the term "ternary compositions" includes compositions comprising one or more, for example 1, 2 or 3, active compounds of the formula I, one or more, for example 1, 2 or 3, safeners of formula II, and one or more, for example 1, 2 or 3, additional herbicides C.

In binary compositions comprising at least one compound of the formula I as component A and at least one safener of formula II as component B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one benzoxazinone compound of the formula I as component A, at least one safener of formula II as component B, and at least one additional herbicide C, the relative proportions by weight of the components A:B are generally in the range of from 1:1000 to 1000:1, preferably in the range of from 1:500 to 500:1, the weight ratio of the components A:C is generally in the range of from 1:1000 to 1000:1, preferably in the range of from 1:500 to 500:1, and the weight ratio of the components B:C is generally in the range of from 1:1000 to 1000:1, preferably in the range of from 1:500 to 500:1.

Particularly preferred optional herbicides C are the herbicides C as defined above; in particular the herbicides C.1-C.143 listed below in table C:

TABLE C

| | Herbicide C |
|---|---|
| C.1 | clethodim |
| C.2 | clodinafop-propargyl |
| C.3 | cycloxydim |
| C.4 | cyhalofop-butyl |
| C.5 | fenoxaprop-P-ethyl |
| C.6 | metamifop |
| C.7 | pinoxaden |
| C.8 | profoxydim |
| C.9 | sethoxydim |
| C.10 | tepraloxydim |
| C.11 | tralkoxydim |
| C.12 | esprocarb |
| C.13 | ethofumesate |
| C.14 | molinate |
| C.15 | prosulfocarb |
| C.16 | thiobencarb |
| C.17 | triallate |
| C.18 | bensulfuron-methyl |
| C.19 | bispyribac-sodium |
| C.20 | cloransulam |
| C.21 | chlorsulfuron |
| C.22 | clorimuron |
| C.23 | cyclosulfamuron |
| C.24 | diclosulam |
| C.25 | florasulam |
| C.26 | flumetsulam |
| C.27 | flupyrsulfuron-methyl-sodium |
| C.28 | foramsulfuron |
| C.29 | imazamox |
| C.30 | imazapic |
| C.31 | imazapyr |
| C.32 | imazaquin |
| C.33 | imazethapyr |
| C.34 | imazosulfuron |
| C.35 | iodosulfuron-methyl-sodium |
| C.36 | mesosulfuron |
| C.37 | metazosulfuron |

TABLE C-continued

| | Herbicide C |
|---|---|
| C.38 | metsulfuron |
| C.39 | metosulam |
| C.40 | nicosulfuron |
| C.41 | penoxsulam |
| C.42 | propoxycarbazon-sodium |
| C.43 | pyrazosulfuron-ethyl |
| C.44 | pyribenzoxim |
| C.45 | pyriftalid |
| C.46 | pyroxsulam |
| C.47 | rimsulfuron |
| C.48 | sulfosulfuron |
| C.49 | thiencarbazone-methyl |
| C.50 | thifensulfuron |
| C.51 | tribenuron |
| C.52 | tritosulfuron |
| C.53 | ametryne |
| C.54 | atrazine |
| C.55 | bentazon |
| C.56 | bromoxynil |
| C.57 | diuron |
| C.58 | fluometuron |
| C.59 | hexazinone |
| C.60 | isoproturon |
| C.61 | linuron |
| C.62 | metamitron |
| C.63 | metribuzin |
| C.64 | propanil |
| C.65 | simazin |
| C.66 | terbuthylazine |
| C.67 | terbutryn |
| C.68 | paraquat-dichloride |
| C.69 | acifluorfen |
| C.70 | butafenacil |
| C.71 | carfentrazone-ethyl |
| C.72 | flumioxazin |
| C.73 | fomesafen |
| C.74 | oxadiargyl |
| C.75 | oxyfluorfen |
| C.76 | saflufenacil |
| C.77 | sulfentrazone |
| C.78 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| C.79 | 3-[7-fluoro-3-oxo-4-(prop-2-ynyl)-3,4-dihydro-2H-benzo[1,4]-oxazin-6-yl]-1,5-dimethyl-6-thioxo-[1,3,5]triazinan-2,4-dione |
| C.80 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| C.81 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| C.82 | benzobicyclon |
| C.83 | clomazone |
| C.84 | diflufenican |
| C.85 | flurochloridone |
| C.86 | isoxaflutole |
| C.87 | mesotrione |
| C.88 | norflurazon |
| C.89 | picolinafen |
| C.90 | sulcotrione |
| C.91 | tefuryltrione |
| C.92 | tembotrione |
| C.93 | topramezone |
| C.94 | bicyclopyrone |
| C.95 | amitrole |
| C.96 | fluometuron |
| C.97 | glyphosate |
| C.98 | glyphosate-isopropylammonium |
| C.99 | glyphosate-trimesium (sulfosate) |
| C.100 | glufosinate |

TABLE C-continued

| | Herbicide C |
|---|---|
| C.101 | glufosinate-P |
| C.102 | glufosinate-ammonium |
| C.103 | pendimethalin |
| C.104 | trifluralin |
| C.105 | acetochlor |
| C.106 | butachlor |
| C.107 | cafenstrole |
| C.108 | dimethenamid-P |
| C.109 | fentrazamide |
| C.110 | flufenacet |
| C.111 | mefenacet |
| C.112 | metazachlor |
| C.113 | metolachlor |
| C.114 | S-metolachlor |
| C.115 | pretilachlor |
| C.116 | fenoxasulfone |
| C.117 | isoxaben |
| C.118 | pyroxasulfone |
| C.119 | 2,4-D |
| C.120 | aminopyralid |
| C.121 | clopyralid |
| C.122 | dicamba |
| C.123 | fluroxypyr-meptyl |
| C.124 | MCPA |
| C.125 | quinclorac |
| C.126 | quinmerac |
| C.127 | aminocyclopyrachlor |
| C.128 | diflufenzopyr |
| C.129 | diflufenzopyr-sodium |
| C.130 | dymron |
| C.131 | indanofan |
| C.132 | indaziflam |
| C.133 | oxaziclomefone |
| C.134 | triaziflam |
| C.135 | II.1 |
| C.136 | II.2 |
| C.137 | II.3 |
| C.138 | II.4 |
| C.139 | II.5 |
| C.140 | II.6 |
| C.141 | II.7 |
| C.142 | II.8 |
| C.143 | II.9 |

The weight ratios of the individual components in the preferred mixtures mentioned below are within the limits given above, in particular within the preferred limits.

Particularly preferred are the compositions 1.1 to 1.143 mentioned below, comprising the benzoxzinone I.a.35, the safener II.a.12 and the substance(s) as defined in the respective row of table 1 especially preferred comprising as only active compounds the benzoxzinone I.a.35, the safener II.a.12 and the substance(s) as defined in the respective row of table 1:

TABLE 1

(compositions 1.1 to 1.143):

| comp. no. | herbicide C |
|---|---|
| 1.1 | C.1 |
| 1.2 | C.2 |
| 1.3 | C.3 |
| 1.4 | C.4 |
| 1.5 | C.5 |
| 1.6 | C.6 |
| 1.7 | C.7 |
| 1.8 | C.8 |
| 1.9 | C.9 |
| 1.10 | C.10 |
| 1.11 | C.11 |
| 1.12 | C.12 |
| 1.13 | C.13 |
| 1.14 | C.14 |
| 1.15 | C.15 |
| 1.16 | C.16 |
| 1.17 | C.17 |
| 1.18 | C.18 |
| 1.19 | C.19 |
| 1.20 | C.20 |
| 1.21 | C.21 |
| 1.22 | C.22 |
| 1.23 | C.23 |
| 1.24 | C.24 |
| 1.25 | C.25 |
| 1.26 | C.26 |
| 1.27 | C.27 |
| 1.28 | C.28 |
| 1.29 | C.29 |
| 1.30 | C.30 |
| 1.31 | C.31 |
| 1.32 | C.32 |
| 1.33 | C.33 |
| 1.34 | C.34 |
| 1.35 | C.35 |
| 1.36 | C.36 |
| 1.37 | C.37 |
| 1.38 | C.38 |
| 1.39 | C.39 |
| 1.40 | C.40 |
| 1.41 | C.41 |
| 1.42 | C.42 |
| 1.43 | C.43 |
| 1.44 | C.44 |
| 1.45 | C.45 |
| 1.46 | C.46 |
| 1.47 | C.47 |
| 1.48 | C.48 |
| 1.49 | C.49 |
| 1.50 | C.50 |
| 1.51 | C.51 |
| 1.52 | C.52 |
| 1.53 | C.53 |
| 1.54 | C.54 |
| 1.55 | C.55 |
| 1.56 | C.56 |
| 1.57 | C.57 |
| 1.58 | C.58 |
| 1.59 | C.59 |
| 1.60 | C.60 |
| 1.61 | C.61 |
| 1.62 | C.62 |
| 1.63 | C.63 |
| 1.64 | C.64 |
| 1.65 | C.65 |
| 1.66 | C.66 |
| 1.67 | C.67 |
| 1.68 | C.68 |
| 1.69 | C.69 |
| 1.70 | C.70 |
| 1.71 | C.71 |
| 1.72 | C.72 |
| 1.73 | C.73 |
| 1.74 | C.74 |
| 1.75 | C.75 |
| 1.76 | C.76 |
| 1.77 | C.77 |
| 1.78 | C.78 |
| 1.79 | C.79 |
| 1.80 | C.80 |
| 1.81 | C.81 |
| 1.82 | C.82 |
| 1.83 | C.83 |
| 1.84 | C.84 |
| 1.85 | C.85 |
| 1.86 | C.86 |
| 1.87 | C.87 |

TABLE 1-continued (compositions 1.1 to 1.143):

| comp. no. | herbicide C |
|---|---|
| 1.88 | C.88 |
| 1.89 | C.89 |
| 1.90 | C.90 |
| 1.91 | C.91 |
| 1.92 | C.92 |
| 1.93 | C.93 |
| 1.94 | C.94 |
| 1.95 | C.95 |
| 1.96 | C.96 |
| 1.97 | C.97 |
| 1.98 | C.98 |
| 1.99 | C.99 |
| 1.100 | C.100 |
| 1.101 | C.101 |
| 1.102 | C.102 |
| 1.103 | C.103 |
| 1.104 | C.104 |
| 1.105 | C.105 |
| 1.106 | C.106 |
| 1.107 | C.107 |
| 1.108 | C.108 |
| 1.109 | C.109 |
| 1.110 | C.110 |
| 1.111 | C.111 |
| 1.112 | C.112 |
| 1.113 | C.113 |
| 1.114 | C.114 |
| 1.115 | C.115 |
| 1.116 | C.116 |
| 1.117 | C.117 |
| 1.118 | C.118 |
| 1.119 | C.119 |
| 1.120 | C.120 |
| 1.121 | C.121 |
| 1.122 | C.122 |
| 1.123 | C.123 |
| 1.124 | C.124 |
| 1.125 | C.125 |
| 1.126 | C.126 |
| 1.127 | C.127 |
| 1.128 | C.128 |
| 1.129 | C.129 |
| 1.130 | C.130 |
| 1.131 | C.131 |
| 1.132 | C.132 |
| 1.133 | C.133 |
| 1.134 | C.134 |
| 1.135 | C.135 |
| 1.136 | C.136 |
| 1.137 | C.137 |
| 1.138 | C.138 |
| 1.139 | C.139 |
| 1.140 | C.140 |
| 1.141 | C.141 |
| 1.142 | C.142 |
| 1.143 | C.143 |

The specific number for each single composition is deductible as follows:

Composition 1.77 for example comprises the compound I.a.35, the safener II.a.12 and sulfentrazone (C.77) (see table 1, entry 1.77; as well as table C, entry C.77.

Composition 7.77 for example comprises imazaquin (C.32) (see the definition for compositions 7.1 to 7.143 below), and the compound I.a.35, the safener II.a.12 and sulfentrazone (C.77) (see table 1, entry 1.77; as well as table C, entry C.77).

Also especially preferred are compositions 2.1. to 2.143 which differ from the corresponding compositions 1.1 to 1.143 only in that they additionally comprise C.2 as further herbicide C.

Also especially preferred are compositions 3.1. to 3.143 which differ from the corresponding compositions 1.1 to 1.143 only in that they additionally comprise C.7 as further herbicide C.

Also especially preferred are compositions 4.1. to 4.143 which differ from the corresponding compositions 1.1 to 1.143 only in that they additionally comprise C.29 as further herbicide C.

Also especially preferred are compositions 5.1. to 5.143 which differ from the corresponding compositions 1.1 to 1.143 only in that they additionally comprise C.30 as further herbicide C.

Also especially preferred are compositions 6.1. to 6.143 which differ from the corresponding compositions 1.1 to 1.143 only in that they additionally comprise C.31 as further herbicide C.

Also especially preferred are compositions 7.1. to 7.143 which differ from the corresponding compositions 1.1 to 1.143 only in that they additionally comprise C.32 as further herbicide C.

Also especially preferred are compositions 8.1. to 8.143 which differ from the corresponding compositions 1.1 to 1.143 only in that they additionally comprise C.33 as further herbicide C.

Also especially preferred are compositions 9.1. to 9.143 which differ from the corresponding compositions 1.1 to 1.143 only in that they additionally comprise C.40 as further herbicide C.

Also especially preferred are compositions 10.1. to 10.143 which differ from the corresponding compositions 1.1 to 1.143 only in that they additionally comprise C.44 as further herbicide C.

Also especially preferred are compositions 12.1. to 12.143 which differ from the corresponding compositions 1.1 to 1.143 only in that they additionally comprise B.45 as further herbicide B.

Also especially preferred are compositions 12.1. to 12.143 which differ from the corresponding compositions 1.1 to 1.143 only in that they additionally comprise C.52 as further herbicide C.

Also especially preferred are compositions 13.1. to 13.143 which differ from the corresponding compositions 1.1 to 1.143 only in that they additionally comprise C.53 as further herbicide C.

Also especially preferred are compositions 14.1. to 14.143 which differ from the corresponding compositions 1.1 to 1.143 only in that they additionally comprise C.54 as further herbicide C.

Also especially preferred are compositions 15.1. to 15.143 which differ from the corresponding compositions 1.1 to 1.143 only in that they additionally comprise C.55 as further herbicide C.

Also especially preferred are compositions 16.1. to 16.143 which differ from the corresponding compositions 1.1 to 1.143 only in that they additionally comprise C.56 as further herbicide C.

Also especially preferred are compositions 17.1. to 17.143 which differ from the corresponding compositions 1.1 to 1.143 only in that they additionally comprise C.57 as further herbicide C.

Also especially preferred are compositions 18.1. to 18.143 which differ from the corresponding compositions 1.1 to 1.143 only in that they additionally comprise C.60 as further herbicide C.

Also especially preferred are compositions 19.1. to 19.143 which differ from the corresponding compositions 1.1 to 1.143 only in that they additionally comprise C.65 as further herbicide C.

Also especially preferred are compositions 20.1. to 20.143 which differ from the corresponding compositions 1.1 to 1.143 only in that they additionally comprise C.66 as further herbicide C.

Also especially preferred are compositions 21.1. to 21.143 which differ from the corresponding compositions 1.1 to 1.143 only in that they additionally comprise C.69 as further herbicide C.

Also especially preferred are compositions 22.1. to 22.143 which differ from the corresponding compositions 1.1 to 1.143 only in that they additionally comprise C.72 as further herbicide C.

Also especially preferred are compositions 23.1. to 23.143 which differ from the corresponding compositions 1.1 to 1.143 only in that they additionally comprise C.73 as further herbicide C.

Also especially preferred are compositions 24.1. to 24.143 which differ from the corresponding compositions 1.1 to 1.143 only in that they additionally comprise C.76 as further herbicide C.

Also especially preferred are compositions 25.1. to 25.143 which differ from the corresponding compositions 1.1 to 1.143 only in that they additionally comprise C.77 as further herbicide C.

Also especially preferred are compositions 26.1. to 26.143 which differ from the corresponding compositions 1.1 to 1.143 only in that they additionally comprise C.82 as further herbicide C.

Also especially preferred are compositions 27.1. to 27.143 which differ from the corresponding compositions 1.1 to 1.143 only in that they additionally comprise C.83 as further herbicide C.

Also especially preferred are compositions 28.1. to 28.143 which differ from the corresponding compositions 1.1 to 1.143 only in that they additionally comprise C.86 as further herbicide C.

Also especially preferred are compositions 29.1. to 29.143 which differ from the corresponding compositions 1.1 to 1.143 only in that they additionally comprise C.86 and C.54 as further herbicides C.

Also especially preferred are compositions 30.1. to 30.143 which differ from the corresponding compositions 1.1 to 1.143 only in that they additionally comprise C.86 and C.60 as further herbicides C.

Also especially preferred are compositions 31.1. to 31.143 which differ from the corresponding compositions 1.1 to 1.143 only in that they additionally comprise C.86 and C.66 as further herbicides C.

Also especially preferred are compositions 32.1. to 32.143 which differ from the corresponding compositions 1.1 to 1.143 only in that they additionally comprise C.87 as further herbicide C.

Also especially preferred are compositions 33.1. to 33.143 which differ from the corresponding compositions 1.1 to 1.143 only in that they additionally comprise C.87 and C.54 as further herbicides C.

Also especially preferred are compositions 34.1. to 34.143 which differ from the corresponding compositions 1.1 to 1.143 only in that they additionally comprise C.87 and C.60 as further herbicides C.

Also especially preferred are compositions 35.1. to 35.143 which differ from the corresponding compositions 1.1 to 1.143 only in that they additionally comprise C.87 and C.66 as further herbicides C.

Also especially preferred are compositions 36.1. to 36.143 which differ from the corresponding compositions 1.1 to 1.143 only in that they additionally comprise C.89 as further herbicide C.

Also especially preferred are compositions 37.1. to 37.143 which differ from the corresponding compositions 1.1 to 1.143 only in that they additionally comprise C.90 as further herbicide C.

Also especially preferred are compositions 38.1. to 38.143 which differ from the corresponding compositions 1.1 to 1.143 only in that they additionally comprise C.90 and C.54 as further herbicides C.

Also especially preferred are compositions 39.1. to 39.143 which differ from the corresponding compositions 1.1 to 1.143 only in that they additionally comprise C.90 and C.60 as further herbicides C.

Also especially preferred are compositions 40.1. to 40.143 which differ from the corresponding compositions 1.1 to 1.143 only in that they additionally comprise C.90 and C.66 as further herbicides C.

Also especially preferred are compositions 41.1. to 41.143 which differ from the corresponding compositions 1.1 to 1.143 only in that they additionally comprise C.92 as further herbicide C.

Also especially preferred are compositions 42.1. to 42.143 which differ from the corresponding compositions 1.1 to 1.143 only in that they additionally comprise C.93 as further herbicide C.

Also especially preferred are compositions 43.1. to 43.143 which differ from the corresponding compositions 1.1 to 1.143 only in that they additionally comprise C.93 and C.54 as further herbicides C.

Also especially preferred are compositions 44.1. to 44.143 which differ from the corresponding compositions 1.1 to 1.143 only in that they additionally comprise C.93 and C.60 as further herbicides C.

Also especially preferred are compositions 45.1. to 45.143 which differ from the corresponding compositions 1.1 to 1.143 only in that they additionally comprise C.93 and C.66 as further herbicides C.

Also especially preferred are compositions 46.1. to 46.143 which differ from the corresponding compositions 1.1 to 1.143 only in that they additionally comprise C.97 as further herbicide C.

Also especially preferred are compositions 47.1. to 47.143 which differ from the corresponding compositions 1.1 to 1.143 only in that they additionally comprise C.97 and C.54 as further herbicides C.

Also especially preferred are compositions 48.1. to 48.143 which differ from the corresponding compositions 1.1 to 1.143 only in that they additionally comprise C.97 and C.76 as further herbicides C.

Also especially preferred are compositions 49.1. to 49.143 which differ from the corresponding compositions 1.1 to 1.143 only in that they additionally comprise C.97 and C.86 as further herbicides C.

Also especially preferred are compositions 50.1. to 50.143 which differ from the corresponding compositions 1.1 to 1.143 only in that they additionally comprise C.97 and C.105 as further herbicides C.

Also especially preferred are compositions 51.1. to 51.143 which differ from the corresponding compositions 1.1 to 1.143 only in that they additionally comprise C.97 and C.87 as further herbicides C.

Also especially preferred are compositions 52.1. to 52.143 which differ from the corresponding compositions 1.1 to 1.143 only in that they additionally comprise C.97 and C.90 as further herbicides C.

Also especially preferred are compositions 53.1. to 53.143 which differ from the corresponding compositions 1.1 to 1.143 only in that they additionally comprise C.97 and B.93 as further herbicides C.

Also especially preferred are compositions 54.1. to 54.143 which differ from the corresponding compositions 1.1 to 1.143 only in that they additionally comprise C.100 as further herbicide C.

Also especially preferred are compositions 55.1. to 55.143 which differ from the corresponding compositions 1.1 to 1.143 only in that they additionally comprise C.103 as further herbicide C.

Also especially preferred are compositions 56.1. to 56.143 which differ from the corresponding compositions 1.1 to 1.143 only in that they additionally comprise C.105 as further herbicide C.

Also especially preferred are compositions 57.1. to 57.143 which differ from the corresponding compositions 1.1 to 1.143 only in that they additionally comprise C.108 as further herbicide C.

Also especially preferred are compositions 58.1. to 58.143 which differ from the corresponding compositions 1.1 to 1.143 only in that they additionally comprise C.109 as further herbicide C.

Also especially preferred are compositions 59.1. to 59.143 which differ from the corresponding compositions 1.1 to 1.143 only in that they additionally comprise C.110 as further herbicide C.

Also especially preferred are compositions 60.1. to 60.143 which differ from the corresponding compositions 1.1 to 1.143 only in that they additionally comprise C.112 as further herbicide C.

Also especially preferred are compositions 61.1. to 61.143 which differ from the corresponding compositions 1.1 to 1.143 only in that they additionally comprise C.114 as further herbicide C.

Also especially preferred are compositions 62.1. to 62.143 which differ from the corresponding compositions 11.1 to 1.143 only in that they additionally comprise C.115 as further herbicide C.

Also especially preferred are compositions 63.1. to 63.143 which differ from the corresponding compositions 1.1 to 1.143 only in that they additionally comprise C.119 as further herbicide C.

Also especially preferred are compositions 64.1. to 64.143 which differ from the corresponding compositions 1.1 to 1.143 only in that they additionally comprise C.121 as further herbicide C.

Also especially preferred are compositions 65.1. to 65.143 which differ from the corresponding compositions 1.1 to 1.143 only in that they additionally comprise C.122 as further herbicide C.

Also especially preferred are compositions 66.1. to 66.143 which differ from the corresponding compositions 1.1 to 1.143 only in that they additionally comprise C.124 as further herbicide C.

Also especially preferred are compositions 67.1. to 67.143 which differ from the corresponding compositions 1.1 to 1.143 only in that they additionally comprise C.125 as further herbicide C.

Also especially preferred are compositions 68.1. to 68.143 which differ from the corresponding compositions 1.1 to 1.143 only in that they additionally comprise C.132 as further herbicide C.

Also especially preferred are compositions 69.1. to 69.143 which differ from the corresponding compositions 1.1 to 1.143 only in that they additionally comprise C.6 as further herbicide C.

Also especially preferred are compositions 70.1. to 70.143 which differ from the corresponding compositions 1.1 to 1.143 only in that they additionally comprise C.14 as further herbicide C.

Also especially preferred are compositions 71.1. to 71.143 which differ from the corresponding compositions 1.1 to 1.143 only in that they additionally comprise C.23 as further herbicide C.

Also especially preferred are compositions 72.1. to 72.143 which differ from the corresponding compositions 1.1 to 1.143 only in that they additionally comprise C.38 as further herbicide C.

Also especially preferred are compositions 73.1. to 73.143 which differ from the corresponding compositions 1.1 to 1.143 only in that they additionally comprise C.76 and C.103 as further herbicides C.

Also especially preferred are compositions 74.1. to 74.143 which differ from the corresponding compositions 1.1 to 1.143 only in that they additionally comprise C.76 and C.105 as further herbicides C.

Also especially preferred are compositions 75.1. to 75.143 which differ from the corresponding compositions 1.1 to 1.143 only in that they additionally comprise C.76 and C.108 as further herbicides C.

Also especially preferred are compositions 76.1. to 76.143 which differ from the corresponding compositions 1.1 to 1.143 only in that they additionally comprise C.76 and C.118 as further herbicides C.

Also especially preferred are compositions 77.1. to 77.143 which differ from the corresponding compositions 1.1 to 1.143 only in that they additionally comprise C.91 as further herbicide C.

Also especially preferred are compositions 78.1. to 78.143 which differ from the corresponding compositions 1.1 to 1.143 only in that they additionally comprise C.94 as further herbicide C.

Also especially preferred are compositions 79.1. to 79.143 which differ from the corresponding compositions 1.1 to 1.143 only in that they additionally comprise C.97 and C.29 as further herbicides C.

Also especially preferred are compositions 80.1. to 80.143 which differ from the corresponding compositions 1.1 to 1.143 only in that they additionally comprise C.97 and C.32 as further herbicides C.

Also especially preferred are compositions 81.1. to 81.143 which differ from the corresponding compositions 1.1 to 1.143 only in that they additionally comprise C.97 and C.33 as further herbicides C.

Also especially preferred are compositions 82.1. to 82.143 which differ from the corresponding compositions 1.1 to 1.143 only in that they additionally comprise C.97 and C.38 as further herbicides C.

Also especially preferred are compositions 83.1. to 83.143 which differ from the corresponding compositions 1.1 to 1.143 only in that they additionally comprise C.97 and C.57 as further herbicides C.

Also especially preferred are compositions 84.1. to 84.143 which differ from the corresponding compositions 1.1 to 1.143 only in that they additionally comprise C.97 and C.66 as further herbicides C.

Also especially preferred are compositions 85.1. to 85.143 which differ from the corresponding compositions 1.1 to 1.143 only in that they additionally comprise C.97 and C.94 as further herbicides C.

Also especially preferred are compositions 86.1. to 86.143 which differ from the corresponding compositions 1.1 to 1.143 only in that they additionally comprise C.97 and C.103 as further herbicides C.

Also especially preferred are compositions 87.1. to 87.143 which differ from the corresponding compositions 1.1 to 1.143 only in that they additionally comprise C.97 and C.108 as further herbicides C.

Also especially preferred are compositions 88.1. to 88.143 which differ from the corresponding compositions 1.1 to 1.143 only in that they additionally comprise C.97 and C.113 as further herbicides C.

Also especially preferred are compositions 89.1. to 89.143 which differ from the corresponding compositions 1.1 to 1.143 only in that they additionally comprise C.97 and C.118 as further herbicides C.

Also especially preferred are compositions 90.1. to 90.143 which differ from the corresponding compositions 1.1 to 1.143 only in that they additionally comprise C.97 and C.122 as further herbicides C.

Also especially preferred are compositions 91.1. to 91.143 which differ from the corresponding compositions 1.1 to 1.143 only in that they additionally comprise C.118 as further herbicide C.

According to one embodiment of the invention, in the ready-to-use preparations of herbicidal compositions, i.e. in the compositions according to the invention in the form of crop protection compositions, the components A (benzoxazinone of formula I), B (safener of formula II) and optionally C can be present formulated jointly or separately in suspended, emulsified or dissolved form. The use forms depend entirely on the intended applications.

Accordingly, a first embodiment of the invention relates to compositions in the form of a crop protection composition formulated as a 1-formulation (component) composition comprising the at least one active compound of the formula I (active compound A) and at least one safener of the formula II (compound B) and optionally at least one further herbicide C, and also a solid or liquid carrier and, if appropriate, one or more surfactants.

Accordingly, a second embodiment of the invention relates to compositions in the form of a crop protection composition formulated as a 2-formulation (component) composition comprising a first formulation (component) comprising the at least one active compound A, at least one compound B, a solid or liquid carrier and, if appropriate, one or more surfactants, and a second component comprising at least one further active compound selected from the herbicides B and safeners C, a solid or liquid carrier and, if appropriate, one or more surfactants.

Accordingly, a third embodiment of the invention relates to compositions in the form of a crop protection composition formulated as a 2-formulation (component) composition comprising a first formulation (component) comprising the at least one active compound A, a solid or liquid carrier and, if appropriate, one or more surfactants, and a second component comprising at least one further active compound selected from the safener of the formula II, a solid or liquid carrier and, if appropriate, one or more surfactants.

The compounds A, B and the optional further compound C can be formulated and applied jointly or separately, simultaneously or in succession, before, during or after the emergence of the plants. In case of separate application, the order of the application of the compounds A, B and optionally C and is of minor importance. The only thing that is important is that the compound A and B and the optional further compound C are present simultaneously at the site of action, i.e. are at the same time in contact with or taken up by the unwanted plant to be controlled and/or the crop to be safened.

In the methods of the present invention it is immaterial whether components A (the benzoxazinone of formula I), B (the safener of formula II) and the optionally further herbicide component C are formulated and applied jointly or separately.

In the case of separate application it is of minor importance, in which order the application takes place. It is only necessary, that the herbicide compound A and the compound B and optionally the herbicide compound C are applied in a time frame that allows simultaneous action of the active ingredients on the plants, preferably within a time-frame of at most 14 days, in particular at most 7 days.

The required application rate of pure active compound composition, i.e. A and B and, if appropriate, C without formulation auxiliaries depends on the composition of the plant stand, on the development stage of the plants, on the climatic conditions at the site of use and on the application technique. In general, the application rate of A and B and, if appropriate, C is from 0.001 to 3 kg/ha, preferably from 0.005 to 2.5 kg/ha and in particular from 0.01 to 2 kg/ha of active substance (a.s.).

According to one embodiment of the invention the required application rates of benzoxaziones I, are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safener II are generally in the range of from 0.0005 kg/ha to 2.5 kg/ha and preferably in the range of from 0.005 kg/ha to 2 kg/ha or 0.01 kg/ha to 1.5 kg/h of a.s.

The application rates of optional herbicides C are generally in the range of from 0.0005 kg/ha to 2.5 kg/ha and preferably in the range of from 0.005 kg/ha to 2 kg/ha or 0.01 kg/ha to 1.5 kg/h of a.s.

The compositions according to the invention are applied to the plants mainly by spraying the leaves. Here, the application can be carried out using, for example, water as carrier by customary spraying techniques using spray liquor amounts of from about 100 to 2000 l/ha (for example from 300 to 400 l/ha). The herbicidal compositions may also be applied by the low-volume or the ultra-low-volume method, or in the form of microgranules.

Application of the herbicidal compositions according to the present invention can be done before, during and/or after, preferably during and/or after, the emergence of the undesirable plants.

The herbicidal compositions according to the present invention can be applied pre- or post-emergence, pre-plant, or together with the seed of a crop plant. It is also possible to apply the compounds and compositions by applying seed, pretreated with a composition of the invention, of a crop plant. If the compounds A and B and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

Hereinbelow, the preparation of the benzoxazinones of the formula I is illustrated by examples; however, the subject matter of the present invention is not limited to the examples given.

EXAMPLE 1

1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

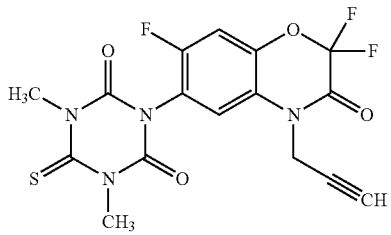

4.1: 2-amino-5-fluorophenol

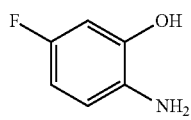

To 5-fluoro-2-nitrophenol (26.63 g, 170 mmol) in Ethanol (250 ml) under $N_2$ atmosphere was added palladium on carbon (10 wt %, 250 mg, 0.235 mmol). The mixture was flushed with $H_2$ and stirred at RT under $H_2$ (balloon) until complete conversion according to thin layer chromatography (TLC) analysis. Pd/C was removed by filtration and the filtrate was concentrated to yield 21.6 g of the title compound.

$^1$H NMR (DMSO): 4.5 (br, 2H); 6.35 (dd, 1H); 6.45 (dd, 1H); 6.50 (dd, 1H); 9.5 (br, 1H).

4.2: 2-bromo-2,2-difluoro-N-(4-fluoro-2-hydroxyphenyl)acetamide

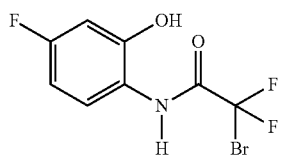 [SMILES: O=C(Nc1ccc(F)cc1O)C(F)(F)Br]

Alternative a)

To 2-amino-5-fluorophenol (14 g, 110 mmol) in dry Tetrahydrofuran at 0° C. was added sodium hydride (55 wt % in mineral oil; 4.81 g, 110 mmol). The resulting mixture was stirred for 15 minutes at −15° C. Subsequently ethyl 2-bromo-2,2-difluoroacetate (24.59 g, 121 mmol) was added dropwise and the resulting mixture was stirred at 0° C. for two hours. The reaction mixture was quenched with saturated aqueous $NH_4Cl$ solution and extracted with ethyl acetate. The combined extracts were washed with brine, dried with $Na_2SO_4$ and concentrated to yield 33 g of the title compound.

$^1$H NMR (DMSO): 3.3 (br, 1H); 6.8 (m, 2H); 7.25 (dd, 1H); 10.4 (br, 1H).

Alternative b)

To 2-amino-5-fluorophenol (200 mg, 1.573 mmol) in dry Tetrahydrofuran at 0° C. was added sodium hydride (55 wt % in mineral oil, 68.6 mg, 1.573 mmol). The resulting mixture was stirred for 15 minutes at −15° C. Subsequently methyl 2-bromo-2,2-difluoroacetate (327 mg, 1.731 mmol) was added dropwise and the resulting mixture was stirred at 0° C. for two hours. The reaction mixture was quenched in saturated aqueous $NH_4Cl$ solution and extracted with ethyl acetate. The combined extracts were washed with brine, dried with $Na_2SO_4$ and concentrated to yield 450 mg of the title compound $^1$H NMR (DMSO): 3.3 (br, 1H); 6.8 (m, 2H); 7.25 (dd, 1H); 10.4 (br, 1H).

4.3: 2,2,7-trifluoro-2H-benzo[b][1,4]oxazin-3(4H)-one

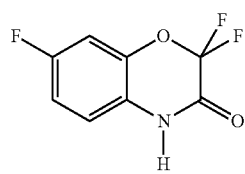

To 2-bromo-2,2-difluoro-N-(4-fluoro-2-hydroxyphenyl)acetamide (33 g, 116 mmol) in dry Toluene was added 1,8-Diazabicyclo[5.4.0]undec-7-en (DBU, 17.51 ml, 116 mmol). The resulting mixture was stirred overnight at 80° C. The reaction was quenched in saturated aqueous $NH_4Cl$ solution and extracted with ethyl acetate. The combined extracts were washed with brine, dried with $Na_2SO_4$ and concentrated to afford 24.94 g of the title compound.

GCMS m/e (M+)=203

4.4: 2,2,7-trifluoro-6-nitro-2H-benzo[b][1,4]oxazin-3(4H)-one

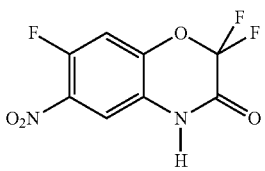 [SMILES: O=C1Nc2cc([N+](=O)[O-])c(F)cc2OC1(F)F]

2,2,7-trifluoro-2H-benzo[b][1,4]oxazin-3(4H)-one (2.5 g, 12.31 mmol) was dissolved in sulfuric acid (40 ml, 750 mmol). The reaction mixture was cooled to 0-5° C. Slowly nitric acid (1.761 ml, 39.7 mmol) was added dropwise and the temperature was maintained between 0-5° C. The reaction mixture was stirred for 30 min at this temperature. Then the reaction mixture was added dropwise to vigorously stirred cold water. A solid was formed, extraction with Dichloromethane. The combined extracts were dried over $Na_2SO_4$, and concentrated to yield 2.56 g of the title compound as brown solid.

GC/MS m/e (M+)=248

1H-NMR (CDCl$_3$): 2.9 (br, 1H); 7.15 (d, 1H); 7.80 (d, 1H).

4.5: 2,2,7-trifluoro-6-nitro-4-(prop-2-ynyl)-2Hbenzo[b][1,4]oxazin-3(4H)-one

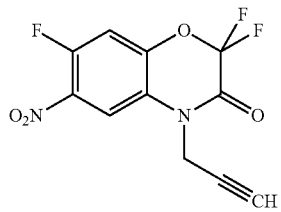 [SMILES: C#CCN1C(=O)C(F)(F)Oc2cc(F)c([N+](=O)[O-])cc21]

To 2,2,7-trifluoro-6-nitro-2H-benzo[b][1,4]oxazin-3(4H)-one (6.9 g, 27.8 mmol) and potassium carbonate (4.61 g, 33.4 mmol) in dry N,N-Dimethylformamide at RT was dropwise added 3-bromoprop-1-yne (80 wt % in toluene; 4.96 g, 33.4 mmol). The resulting mixture was stirred at RT overnight. The reaction mixture was poured in saturated aqueous NH$_4$Cl solution and extracted with ethyl acetate. The combined extracts were washed with aqueous NaCl solution, dried with Na$_2$SO$_4$, concentrated and chased with toluene to yield 7.06 g of the title compound as dark brown solid.

GCMS m/e (M+)=286

4.6: 6-amino-2,2,7-trifluoro-4-(prop-2-ynyl)-2Hbenzo[b][1,4]oxazin-3(4H)-one

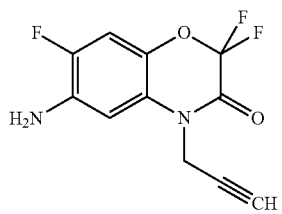

To ammonium chloride (3.96 g, 74.0 mmol) in water was added iron powder (325 mesh; 4.13 g, 74.0 mmol). To the resulting mixture was added 2,2,7-trifluoro-6-nitro-4-(prop-2-ynyl)-2Hbenzo[b][1,4]oxazin-3(4H)-one (7.06 g, 24.67 mmol) in methanol/tetrahydrofuran. The resulting mixture was stirred vigorously at 70° C. for 2 hours. The reaction was quenched in water/ethyl acetate under stirring. The resulting 2 phase system was filtered and the layers were separated. The water layer was subsequently extracted with ethyl acetate. The combined organic phases were washed with brine, dried with Na$_2$SO$_4$ and concentrated to yield 5.15 g of the title compound.

GCMS m/e (M+)=256

4.7: 2,2,7-trifluoro-6-isocyanato-4-(prop-2-ynyl)-2Hbenzo[b][1,4]oxazin-3(4H)-one

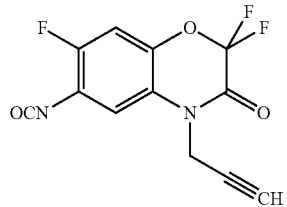

To 6-amino-2,2,7-trifluoro-4-(prop-2-ynyl)-2H-benzo[b][1,4]oxazin-3(4H)-one (5.1 g, 19.91 mmol) in dry toluene was dropwise added diphosgene (2.64 ml, 21.90 mmol) in dry toluene. The resulting mixture was stirred overnight at reflux. Concentrated and chased with toluene and used as such in the next step.

4.8: 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

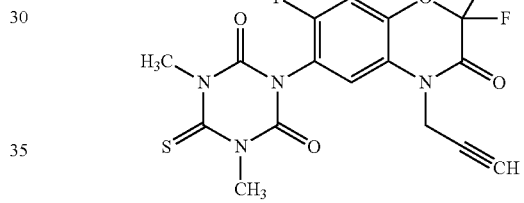

To 1,3-dimethylthiourea (2.489 g, 23.89 mmol) and triethylamine (2.78 ml, 19.91 mmol) in dry toluene was added 2,2,7-trifluoro-6-isocyanato-4-(prop-2-ynyl)-2H-benzo[b][1,4]oxazin-3(4H)-one (5.62 g, 19.91 mmol) in dry toluene. Hereto was subsequently added carbonyldiimidazole (CDI; 6.46 g, 39.8 mmol) and the resulting mixture was stirred at 80° C. overnight. Then the reaction mixture was cooled to room temperature and poured into ethyl acetate/water under stirring. The layers were separated and the aqueous layer was extracted with dichloromethane. The combined extracts were washed with brine, dried with Na$_2$SO$_4$ and concentrated to yield 14.4 g.

This residue was stirred in dichloromethane/methanol, the precipitate was isolated over glass filter. The filtrate was concentrated to yield 7.2 g of the title compound.

GCMS m/e (M+)=412

$^1$H-NMR (DMSO): 3.49 (s, 1H); 3.64 (s, 6H); 4.71 (s, 2H); 7.8 (m, 2H).

USE EXAMPLES

The herbicidal effect of the compositions according to the present invention comprising at least a benzoxazinone of formula I and a safener of formula II, and optionally one or more further herbicide(s) C, on the growth of undesirable plants and the safening action on crops was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had emerged. This cover caused uniform germination of the test plants, unless this has been impaired by the active ingredients.

For the post-emergence treatment, the test plants were first grown to a height of 1 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

The respective benzoxazinone of formula I was formulated as a 5% by weight strength emulsion concentrate, and the safener of formula II as a 5% by weight emulsion concentrate. Optional component C can be used in its appropriate available formulation type.

The benzoxazinone of formula I, the safener of formula II, and optional component C were introduced to the spray liquid with the amount of solvent system used for applying the active compound.

The test period extended over 20 days. During this time, the plants were tended, and their response to the treatments with active compound was evaluated.

Depending on the species, the plants were kept at 10-25° C. or 20-35° C. During the test period the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

A safener action is present if the damage to the crop plant caused by a mixture according to the present invention which contains a benzoxazinone of formula I and a safener of formula II is less than the damage caused when the benzoxazinone of formula I (optionally in mixture with a further herbicide C) according to the present invention is used without the safener of formula II.

The plants used in these greenhouse experiments belong to the following species:

| BAYER-Code | Scientific name |
|---|---|
| ZEAMX | *Zea mays* |
| ORYSA | *Oryza sativa* |
| SETFA | *Setaria faberi* |

Example 1

Herbicidal Action of the Pre-Emergence Applied Mixture of Benzoxazinone I.a.35 and Safener II.a.12 Against SETFA and Safener Action with Regard to ZEAMX, TRZAW and ORYSA

| application rate [g/ha] | | damage to crop plant | damage to crop plant | damage to crop plant | herbicidal action against |
|---|---|---|---|---|---|
| I.a.35 | II.a.12 | ZEAMX | TRZAW | ORYSA | SETFA |
| 50 | — | 65 | 65 | 65 | 100 |
| — | 150 | 0 | 0 | 0 | 0 |
| 50 | 150 | 35 | 45 | 55 | 98 |

Example 2

Herbicidal Action of the Pre-Emergence Applied Mixture of Benzoxazinone I.a.35 and Safener II.a.12 Against SETFA and Safener Action with Regard to ZEAMX, TRZAW and ORYSA

| application rate [g/ha] | | damage to crop plant | damage to crop plant | damage to crop plant | herbicidal action against |
|---|---|---|---|---|---|
| I.a.35 | II.a.12 | ZEAMX | TRZAW | ORYSA | SETFA |
| 25 | — | 40 | 60 | 40 | 100 |
| — | 75 | 0 | 0 | 0 | 0 |
| 25 | 75 | 10 | 40 | 35 | 100 |

Example 3

Herbicidal Action of the Pre-Emergence Applied Mixture of Benzoxazinone I.a.35 and Safener II.a.12 Against SETFA and Safener Action with Regard to ZEAMX, TRZAW and ORYSA

| application rate [g/ha] | | damage to crop plant | damage to crop plant | damage to crop plant | herbicidal action against |
|---|---|---|---|---|---|
| I.a.35 | II.a.12 | ZEAMX | TRZAW | ORYSA | SETFA |
| 12.5 | — | 25 | 45 | 30 | 90 |
| — | 150 | 0 | 0 | 0 | 0 |
| 12.5 | 150 | 0 | 0 | 20 | 90 |

Example 4

Herbicidal Action of the Post-Emergence Applied Mixture of Benzoxazinone I.a.35 and Safener II.a.12 Against SETFA and Safener Action with Regard to ORYSA

| application rate [g/ha] | | damage to crop plant | herbicidal action against |
|---|---|---|---|
| I.a.35 | II.a.12 | ORYSA | SETFA |
| 25 | — | 60 | 100 |
| — | 75 | 0 | 0 |
| 25 | 75 | 35 | 100 |

We claim:

1. A composition comprising
A) a benzoxazinone of the formula I

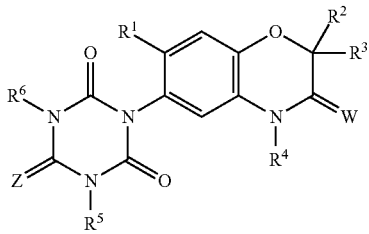

wherein
$R^1$ is hydrogen or halogen;
$R^2$ is halogen;
$R^3$ is halogen;
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is hydrogen, $NH_2$, $C_1$-$C_6$-alkyl or $C_3$-$C_6$-alkynyl;
$R^6$ is hydrogen or $C_1$-$C_6$-alkyl; and
W is O or S; and
Z is O or S; and
B) a safener of formula II

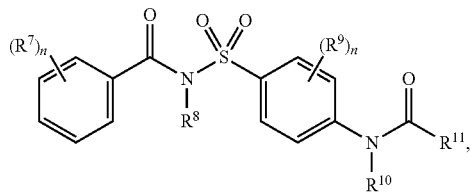

wherein
n is 1 to 5;
$R^7$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^8$ is hydrogen or $C_1$-$C_6$-alkyl;
$R^9$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^{10}$ is hydrogen or $C_1$-$C_6$-alkyl; and
$R^{11}$ is hydrogen, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, $C_1$-$C_6$-alkylthio, $C_1$-$C_6$-alkylamino, di($C_1$-$C_6$-alkyl)amino, $C_3$-$C_6$-cycloalkylamino or $C_3$-$C_6$-cycloalkyl.

2. The composition as claimed in claim 1, wherein $R^1$, $R^2$, $R^4$, $R^5$, $R^6$, W and Z in formula I have the following meaning:
$R^1$ is halogen;
$R^2$ is fluorine;
$R^4$ is $C_3$-$C_6$-alkynyl or $C_3$-$C_6$-halolkynyl;
$R^5$ is $NH_2$, $C_1$-$C_6$-alkyl or $C_3$-$C_6$-alkynyl;
$R^6$ is $C_1$-$C_6$-alkyl;
W is O; and
Z is S.

3. The composition as claimed in claim 1, wherein n, $R^7$, $R^8$, $R^9$, $R^{10}$ and $R^{11}$ in formula II have the following meaning:
n is 1 or 2;
$R^7$ is $C_1$-$C_6$-alkyl or $C_1$-$C_6$-alkoxy;
$R^8$, $R^9$ and $R^{10}$ are hydrogen; and
$R^{11}$ is $C_1$-$C_6$-alkylamino or di($C_1$-$C_6$-alkyl)amino.

4. The composition as claimed in claim 1 comprising as the only herbicidal active compound a benzoxazinone of formula I in combination with the safener of formula II.

5. The composition as claimed in claim 1 comprising a benzoxazinone of formula I, a safener of formula II, and at least one additional herbicide.

6. The composition as claimed in claim 1 in the form of a crop protection composition comprising also auxiliaries customary for formulating crop protection agents.

7. A method for controlling unwanted vegetation in crop plants wherein a herbicidal effective amount of a composition according to claim 1 is applied on plants, their habitat or seed.

8. A method for controlling unwanted vegetation in crop plants comprising applying on the plants, their habitat or seed a herbicidal effective amount of
a benzoxazinone of the formula I

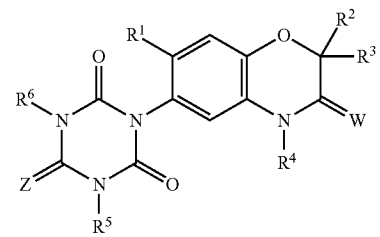

wherein
$R^1$ is hydrogen or halogen;
$R^2$ is halogen;
$R^3$ is halogen;
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is hydrogen, $NH_2$, $C_1$-$C_6$-alkyl or $C_3$-$C_6$-alkynyl;
$R^6$ is hydrogen or $C_1$-$C_6$-alkyl; and
W is O or S; and
Z is O or S; and a safener of formula II

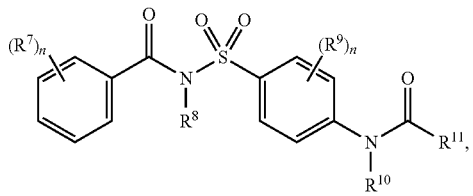

wherein
n is 1 to 5;
$R^7$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^8$ is hydrogen or $C_1$-$C_6$-alkyl;
$R^9$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^{10}$ is hydrogen or $C_1$-$C_6$-alkyl; and
$R^{11}$ is hydrogen, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, $C_1$-$C_6$-alkylthio, $C_1$-$C_6$-alkylamino, di($C_1$-$C_6$-alkyl)amino, $C_3$-$C_6$-cycloalkylamino or $C_3$-$C_6$-cycloalkyl;
wherein compound I and compound II are applied before, during and/or after emergence of the unwanted plants, where the compounds are applied simultaneously or in succession.

9. The method of claim 8, wherein $R^1$, $R^2$, $R^4$, $R^5$, $R^6$, W and Z in formula I have the following meaning:
$R^1$ is halogen;
$R^2$ is fluorine;
$R^4$ is $C_3$-$C_6$-alkynyl or $C_3$-$C_6$-halolkynyl;
$R^5$ is $NH_2$, $C_1$-$C_6$-alkyl or $C_3$-$C_6$-alkynyl;
$R^6$ is $C_1$-$C_6$-alkyl;
W is O; and
Z is S.

10. The method of claim 8, wherein n, $R^7$, $R^8$, $R^9$, $R^{10}$ and $R^{11}$ in formula II have the following meaning:
n is 1 or 2;
$R^7$ is $C_1$-$C_6$-alkyl or $C_1$-$C_6$-alkoxy;
$R^8$, $R^9$ and $R^{10}$ are hydrogen; and
$R^{11}$ is $C_1$-$C_6$-alkylamino or di($C_1$-$C_6$-alkyl)amino.

11. A method of safening the phytotoxic activity of a benzoxazinone of formula I,

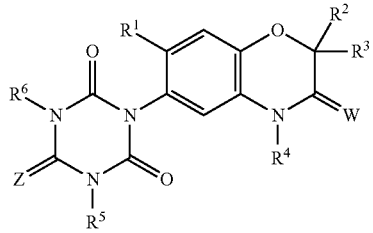

wherein
$R^1$ is hydrogen or halogen;
$R^2$ is halogen;
$R^3$ is halogen;
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is hydrogen, $NH_2$, $C_1$-$C_6$-alkyl or $C_3$-$C_6$-alkynyl;
$R^6$ is hydrogen or $C_1$-$C_6$-alkyl; and
W is O or S; and
Z is O or S; and
which comprises applying said benzoxazinone of formula I in combination with a safener of formula II

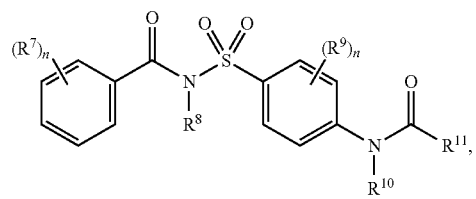

wherein
n is 1 to 5;
$R^7$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^8$ is hydrogen or $C_1$-$C_6$-alkyl;
$R^9$ is hydrogen, halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $NH_2$, carboxyl, carbamoyl, formyl or sulfamoyl;
$R^{10}$ is hydrogen or $C_1$-$C_6$-alkyl; and
$R^{11}$ is hydrogen, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, $C_1$-$C_6$-alkylthio, $C_1$-$C_6$-alkylamino, di($C_1$-$C_6$-alkyl)amino, $C_3$-$C_6$-cycloalkylamino or $C_3$-$C_6$-cycloalkyl;
in an amount effective to reduce the phytotoxic activity of said benzoxazinone of formula I on crop plants.

12. The method of safening as claimed in claim 11, wherein the crop plants are selected from the group consisting of cereals, corn, soybeans, rice, oilseed rape, cotton, potatoes, peanuts, turf grass species and permanent crops.

13. The method of safening as claimed in claim 11, comprising applying as the only herbicidal active compound a benzoxazinone of formula I in combination with the safener of formula II.

14. The method of claim 11, wherein $R^1$, $R^2$, $R^4$, $R^5$, $R^6$, W and Z in formula I have the following meaning:
$R^1$ is halogen;
$R^2$ is fluorine;
$R^4$ is $C_3$-$C_6$-alkynyl or $C_3$-$C_6$-halolkynyl;
$R^5$ is $NH_2$, $C_1$-$C_6$-alkyl or $C_3$-$C_6$-alkynyl;
$R^6$ is $C_1$-$C_6$-alkyl;
W is O; and
Z is S.

15. The method of claim 11, wherein n, $R^7$, $R^8$, $R^9$, $R^{10}$ and $R^{11}$ in formula II have the following meaning:
n is 1 or 2;
$R^7$ is $C_1$-$C_6$-alkyl or $C_1$-$C_6$-alkoxy;
$R^8$, $R^9$ and $R^{10}$ are hydrogen; and
$R^{11}$ is $C_1$-$C_6$-alkylamino or di($C_1$-$C_6$-alkyl)amino.

* * * * *